(12) United States Patent
Imhof et al.

(10) Patent No.: US 8,093,010 B2
(45) Date of Patent: *Jan. 10, 2012

(54) ANGIOGENESIS INHIBITING MOLECULES, THEIR SELECTION, PRODUCTION AND THEIR USE IN THE TREATMENT OF CANCER

(75) Inventors: Beat A. Imhof, Conches (CH); Michel Aurrand-Lions, Marseilles (FR)

(73) Assignee: Merck Serono S.A., Coinsins, Vaud (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/608,029

(22) Filed: Oct. 29, 2009

(65) Prior Publication Data

US 2010/0279307 A1 Nov. 4, 2010

Related U.S. Application Data

(62) Division of application No. 10/738,123, filed on Dec. 18, 2003, now Pat. No. 7,642,341.

(51) Int. Cl.
| | |
|---|---|
| G01N 33/53 | (2006.01) |
| G01N 33/536 | (2006.01) |
| G01N 33/543 | (2006.01) |
| G01N 33/567 | (2006.01) |
| G01N 33/577 | (2006.01) |
| C07K 16/28 | (2006.01) |
| C12N 5/20 | (2006.01) |

(52) U.S. Cl. ...... 435/7.21; 435/7.1; 435/7.93; 435/7.94; 435/7.95; 435/40.5; 435/40.51; 435/40.52; 435/70.21; 435/328; 435/334; 435/344; 436/503; 436/512; 436/518; 436/536; 436/548; 530/387.3; 530/388.22; 530/388.8

(58) Field of Classification Search .................. 435/7.1, 435/7.21, 7.93, 7.94, 7.95, 40.5, 40.51, 40.52, 435/70.21, 328, 334, 344; 436/503, 512, 436/518, 536, 548; 530/387.3, 388.22, 388.8
See application file for complete search history.

(56) References Cited

U.S. PATENT DOCUMENTS

| | | | |
|---|---|---|---|
| 5,545,806 | A | 8/1996 | Lonberg et al. |
| 5,545,807 | A | 8/1996 | Surani et al. |
| 5,569,825 | A | 10/1996 | Lonberg et al. |
| 5,625,126 | A | 4/1997 | Lonberg et al. |
| 5,633,425 | A | 5/1997 | Lonberg et al. |
| 5,661,016 | A | 8/1997 | Lonberg et al. |
| 5,712,120 | A | 1/1998 | Rodriguez et al. |
| 5,770,429 | A | 6/1998 | Lonberg et al. |
| 5,789,650 | A | 8/1998 | Lonberg et al. |
| 5,814,318 | A | 9/1998 | Lonberg et al. |
| 5,874,299 | A | 2/1999 | Lonberg et al. |
| 5,877,397 | A | 3/1999 | Lonberg et al. |
| 6,399,763 | B1 | 6/2002 | Frenken et al. |
| 7,642,341 | B2 * | 1/2010 | Imhof et al. ............ 530/388.22 |
| 7,790,863 | B2 * | 9/2010 | Imhof et al. ............ 530/388.22 |
| 2003/0017534 | A1 | 1/2003 | Buelow et al. |
| 2003/0073149 | A1 * | 4/2003 | Archer et al. ............... 435/7.92 |
| 2004/0208873 | A1 | 10/2004 | Teeling et al. |
| 2005/0136060 | A1 | 6/2005 | Imhof et al. |
| 2005/0266426 | A1 | 12/2005 | Imhof et al. |
| 2007/0202110 | A1 | 8/2007 | Imhof et al. |

FOREIGN PATENT DOCUMENTS

| | | |
|---|---|---|
| EP | 0843961 | 5/1996 |
| WO | WO 92/03918 | 3/1992 |
| WO | WO 92/22645 | 12/1992 |
| WO | WO 93/01227 | 1/1993 |
| WO | WO 94/25585 | 11/1994 |
| WO | WO 97/07671 | 3/1997 |
| WO | WO 98/24884 | 6/1999 |
| WO | WO 99/45962 | 9/1999 |
| WO | WO 2000/053749 | 9/2000 |
| WO | WO 01/14424 | 3/2001 |
| WO | WO 02/43478 | 6/2002 |
| WO | WO 03/006673 A2 | 1/2003 |
| WO | WO 2003/008541 A2 | 1/2003 |
| WO | WO 03/59282 | 7/2003 |
| WO | WO 2004/055056 | 7/2004 |
| WO | WO 2005/050213 | 6/2005 |

OTHER PUBLICATIONS

Li, C. H. et al. "β-Endorphin omission analogs: Dissociation of immunoreactivity from other biological activities", *Proc. Natl. Acad. Sci. USA*, Jun. 1980, pp. 3211-3214, vol. 77, No. 6.

MacCallum, R. M. et al. "Antibody-antigen Interactions: Contact Analysis and Binding Site Topography", *J. Mol. Biol.*, 1996, pp. 732-745, vol. 262.

Lederman, S. et al. "A Single Amino Acid Substitution in a Common African Allele of the CD4 Molecule Ablates Binding of the Monoclonal Antibody, OKT4", *Molecular Immunology*, 1991, pp. 1171-1181, vol. 28, No. 11.

Bendig, M. M. "Humanization of Rodent Monoclonal Antibodies by CDR Grafting", *Methods: A Companion to Methods in Enzymology*, 1995, pp. 83-93, vol. 8.

(Continued)

*Primary Examiner* — Gail R Gabel
*Assistant Examiner* — James L Grun
(74) *Attorney, Agent, or Firm* — Saliwanchik, Lloyd & Eisenschenk

(57) ABSTRACT

The present invention relates to a method for providing molecules that are capable of inhibiting angiogenesis, comprising the steps of providing a range of molecules; testing whether these molecules can prevent interaction between JAM-B and JAM-C; testing the positive molecules for their ability to block angiogenesis in vivo; and selecting molecules that are positive in the angiogenesis test as angiogenesis inhibiting molecules. The method may further comprise the step of isolating or producing the angiogenesis inhibiting molecules. The invention further relates to the angiogenesis inhibiting molecules thus provided and produced, to their use in the treatment of cancer, to therapeutical compositions comprising them. In a particular embodiment the invention relates to monoclonal antibodies, in particular Mab H33, to soluble JAM-C and JAM-B and to small molecules.

12 Claims, 7 Drawing Sheets

OTHER PUBLICATIONS

Colman, P. M. "Effects of amino acid sequence changes on antibody-antigen interactions", *Research in Immunology*, 1994, pp. 33-36.

Casset, F. et al. "A peptide mimetic of an anti-CD4 monoclonal antibody by rational design", *Biochemical and Biophysical Research Communications*, 2003, pp. 198-205, vol. 307.

Taylor, L. D. et al. "Human immunoglobulin transgenes undergo rearrangement, somatic mutation and class switching in mice that lack endogenous IgM", *International Immunology*, 1994, pp. 579-591, vol. 6, No. 4.

Paul, W. E., Fundamental Immunology, 3rd Edition, Chapter 9, Immunoglobulins, Structure and Function, 1993, pp. 284-314, Raven Press, Ltd., New York.

Author Guide—*Blood* (from Internet), 2007, pp. 8-9.

Arrate, M.P. et al. "Cloning of human junctional adhesion molecule 3 (JAM3) and its identification as the JAM2 counter-receptor", *The Journal of Biological Chemistry*, Dec. 7, 2001, pp. 45826-45832, vol. 276, No. 49.

Aurrand-Lions, M. et al. "JAM-2, a novel immunologlobulin superfamily molecule, expressed by endothelial and lymphatic cells", *Journal of Biological Chemistry*, Jan. 26, 2001, pp. 2733-2741, vol. 276, No. 4.

Bazzoni, G. "The JAM family of junctional adhesion molecules", *Current Opinion in Cell Biology*, 2003, pp. 525-530, vol. 15, No. 5.

Johnson-Léger, C. et al. "Junctional adhesion molecule-2 (JAM-2) promotes lymphocyte transendothelial migration", *Blood*, Oct. 1, 2002, pp. 2479-2486, vol. 100, No. 7.

Liang, T. W. et al. "Vascular endothelial-junctional adhesion molecule (VE-JAM)/JAM 2 interacts with T, NK, and dendrittic cells through JAM 3", *Journal of Immunology*, 2002, pp. 1618-1626, vol. 168, No. 4.

Muller, W.A. "Leukocyte—endothelial-cell interactions in leukocyte transmigration and the inflammatory response", *Trends in Immunology*, Jun. 2003, pp. 326-333, vol. 24, No. 6.

Naik, M.U. et al. "Signaling through JAM-1 and $\alpha_v\beta_3$ is required for the angiogenic action of bFGF: dissociation of the JAM-1 and $\alpha_v\beta_3$ complex", *Blood*, Sep. 15, 2003, pp. 2108-2114, vol. 102, No. 6.

Vestweber, D. "Regulation of endothelial cell contacts during leukocyte extravasation", *Current Opinion in Cell Biology*, 2002, pp. 587-593, vol. 14, No. 5.

Vestweber, D. "Molecular mechanisms that control endothelial cell contacts", *Journal of Pathology*, 2000, pp. 281-291, vol. 190, No. 3.

Aurrand-Lions, M. et al. "Heterogeneity of endothelial junctions is reflected by differential expression and specific subcellular localization of the three JAM family members", *Blood*, Dec. 15, 2001, pp. 3699-3707, vol. 98, No. 13.

Chavakis, T. et al. "The junctional adhesion molecule-C promotes neutrophil transendothelial migration in Vitro and in Vivo", *The Journal of Biological Chemistry*, Dec. 31, 2004, pp. 55602-55608, vol. 279, No. 53.

Chen, J. et al. "B cell development in mice that lack one or both immunoglobulin κ light chain genes", *The EMBO Journal*, 1993, pp. 821-830, vol. 12, No. 3.

Chen, J. et al. "Immunoglobulin gene rearrangement in B cell deficient mice generated by targeted deletion of the $J_H$ locus", *International Immunology*, 1993, pp. 647-656, vol. 5, No. 6.

Choi, T.K. et al. "Transgenic mice containing a human heavy chain immunoglobulin gene fragment cloned in a yeast artificial chromosome", *Nature Genetics*, Jun. 1993, pp. 117-123, vol. 4.

Crowther, M. et al. "Microenvironmental influence on macrophage regulation of angiogenesis in wounds and malignant tumors", *Journal of Leukocyte Biology*, Oct. 2001, pp. 478-490, vol. 70.

Cunningham, S.A. et al. "A Novel Protein with Homology to the Junctional Adhesion Molecule", *The Journal of Biological Chemistry*, Nov. 3, 2000, pp. 34750-34756, vol. 275, No. 44.

Fishwild, D.M. et al. "High-avidity human IgGκ monoclonal antibodies from a novel strain of minilocus transgenic mice", *Nature Biotechnology*, Jul. 1996, pp. 845-851, vol. 14.

Harding, F.A. et al. "Class switching in human immunoglobulin transgenic mice", *Annals New York Academy of Sciences*, 1995, pp. 536-546, vol. 764.

Jones, P.T. et al. "Replacing the complementarity-determining regions in a human antibody with those from a mouse", *Nature*, May 29, 1986, pp. 522-525, vol. 321.

Joosten, V. et al. "The production of antibody fragments and antibody fusion proteins by yeasts and filamentous fungi", *Microbial Cell Factories*, 2003, pp. 1-15, vol. 2, No. 1.

Kohler, G. et al. "Continuous cultures of fused cells secreting antibody of predefined specificity", *Nature*, Aug. 7, 1975, pp. 495-497, vol. 256.

Lonberg, N. et al. "Antigen-specific human antibodies from mice comprising four distinct genetic modifications", *Nature*, Apr. 28, 1994, pp. 856-859, vol. 368.

Lonberg, N. et al. "Human antibodies from transgenic mice", *Intern. Rev. Immunol.*, 1995, pp. 65-93, vol. 13.

Lonberg, N. "Transgenic approaches to human monoclonal antibodies", *Handbook of Experimental Pharmacology*, 1994, pp. 49-101, vol. 113.

Merino, R. et al. "The Yαα gene abrogates the major histocompatibility complex association of murine lupus in (NZB ×BXSB)F$_1$ Hybrid Mice", *J. Clin. Invest.*, Aug. 1994, pp. 521-525, vol. 94, No. 2.

Morrison, S.L. et al. "Transfectomas provide novel chimeric antibodies", *Science*, Sep. 20, 1985, pp. 1202-1207, vol. 229.

Murdock, C. et al. "Mechanisms regulating the recruitment of macrophages into hypoxic areas of tumors and other ischemic tissues", *Blood*, Oct. 15, 2004, pp. 2224-2234, vol. 104, No. 8.

Padlan, E.A. "A possible procedure for reducing the immunogenicity of antibody variable domains while preserving their ligand-binding properties", *Molecular Immunology*, 1991, pp. 489-498, vol. 28, No. 4/5.

Padlan, E.A. "Anatomy of the antibody molecule", *Molecular Immunology*, 1994, pp. 169-217, vol. 31, No. 3.

Palmeri, D. et al. "Vascular endothelial junction-associated molecule, a novel member of the immunoglobulin superfamily, is localized to intercellular boundaries of Endothelial Cells", *The Journal of Biological Chemistry*, Jun. 23, 2000, pp. 19139-19145, vol. 275, No. 25.

Queen, C. et al. "A humanized antibody that binds to the interleukin 2 receptor", *Proc. Natl. Acad. Sci. USA*, Dec. 1989, pp. 10029-10033, vol. 86.

Riechmann, L. et al. "Reshaping human antibodies for therapy", *Nature*, Mar. 24, 1988, pp. 323- 327, vol. 332, No. 24.

Taylor, L.D. et al. "A transgenic mouse that expresses a diversity of human sequence heavy and light chain immunoglobulins", *Nucleic Acids Research*, 1992, pp. 6287-6295, vol. 20, No. 23.

Tuaillon, N. et al. "Human immunoglobulin heavy-chain minilocus recombination in transgenic mice: Gene-segment use in μ and γ transcripts", *Proc. Natl. Acad. Sci. USA*, Apr. 1993, pp. 3720-3724, vol. 90.

Tuaillon, N. et al. "Biased utilization of $D_{HQ52}$ and $J_HA$ gene segments in a human Ig transgenic minilocus is independent of antigenic selection", 1994, pp. 2912-2920, vol. 152.

Verhoeyen, M. et al. "Reshaping human antibodies: grafting an antilysozyme activity", *Science*, Mar. 25, 1988, pp. 1534-1536, vol. 239.

Zen, K. et al. "JAM-C is a component of desmosomes and a ligand for CD11b/CD18-mediated neutrophil transepithelial migration", *Molecular Biology of the Cell*, Aug. 2004, pp. 3926-3937, vol. 15.

Antibody/Collaborator Table, Aug. 14, 2002.

O'Brien, S. et al. "Humanization of Monoclonal Antibodies by CDR Grafting", *Methods in Molecular Biology*, 2003, pp. 81-100, vol. 207.

Mountain, A. et al. "Engineering Antibodies for Therapy", *Biotechnology and Genetic Engineering Reviews*, Dec. 1992, pp. 1-142, vol. 10.

de Haard, H. et al. "Creating and engineering human antibodies for immunotherapy", *Advanced Drug Delivery Reviews*, 1998, pp. 5-31, vol. 31.

Figini, M. et al. "Isolation of Human Monoclonal Antibodies Using Guided Selection with Mouse Monoclonal Antibodies", *Methods in Molecular Biology*, 2002, pp. 207-217, vol. 178.

Rader, C. et al. "A phage display approach for rapid antibody humanization: Designed combinatorial V gene libraries", *Proc. Natl. Acad. Sci. USA*, Jul. 1998, pp. 8910-8915, vol. 95.

Klimka, A. et al. "Human anti-CD30 recombinant antibodies by guided phage antibody selection using cell panning", *British Journal of Cancer*, 2000, pp. 252-260, vol. 83, No. 2.

Beiboer, S. et al. "Guided Selection of a Pan Carcinoma Specific Antibody Reveals Similar Binding Characteristics yet Structural Divergence Between the Original Murine Antibody and its Human Equivalent", *J. Mol. Biol.*, 2000, pp. 833-849, vol. 296.

Schmidt, A. et al. "Generation of human high-affinity antibodies specific for the fibroblast activation protein by guided selection", *Eur. J. Biochem.*, 2001, pp. 1730-1738, vol. 268.

Ditzel, H. et al. "Determinants of Polyreactivity in a Large Panel of Recombinant Human Antibodies from HIV-1 Infection", *The Journal of Immunology*, 1996, pp. 739-749, vol. 157.

Rudikoff, et al. "Single amino acid substitution altering antigen-binding specificity" *Proc. Natl. Acad. Sci. USA*, 1982, pp. 1979-1983, vol. 79.

Padlan, et al. "Identification of specificity-determining residues in antibodies" *FASEB Journal*, 1995, pp. 133-139, vol. 9.

* cited by examiner

US 8,093,010 B2

SEQUENCE LISTING

```
<160> NUMBER OF SEQ ID NOS: 3

<210> SEQ ID NO 1
<211> LENGTH: 31
<212> TYPE: DNA
<213> ORGANISM: Homo sapiens

<400> SEQUENCE: 1
gctctagaca gtgttgccgt cttgcctaca g                            31

<210> SEQ ID NO 2
<211> LENGTH: 18
<212> TYPE: DNA
<213> ORGANISM: Homo sapiens
```

```
<400> SEQUENCE: 2
tcagctaggc agccagct                                                18

<210> SEQ ID NO 3
<211> LENGTH: 28
<212> TYPE: DNA
<213> ORGANISM: Homo sapiens

<400> SEQUENCE: 3
gctctagaat ctacttgcat tcgcttcc                                      28
```

ANGIOGENESIS INHIBITING MOLECULES, THEIR SELECTION, PRODUCTION AND THEIR USE IN THE TREATMENT OF CANCER

CROSS-REFERENCE TO RELATED APPLICATIONS

This application is a divisional of U.S. Ser. No. 10/738,123, filed Dec. 18, 2003, now U.S. Pat. No. 7,642,341, the disclosure of which is hereby incorporated by reference in its entirety, including all figures, tables and amino acid or nucleic acid sequences.

BACKGROUND OF THE INVENTION

1. Field of the Invention

The present invention relates to molecules that are capable of inhibiting angiogenesis, to compositions comprising one or more of the molecules, to the use of such molecules in the treatment of carcinoma, in particular solid tumors carcinomas, and to method for providing molecules that are capable of inhibiting angiogenesis.

2. Related Technology

Angiogenesis, the formation of new blood vessels from the pre-existing vasculature is fundamental to wound healing, reproduction and embryonic development. Angiogenesis is also essential for the development of tumors. New blood vessels in tumors provide nutrients allowing the cells to undergo uncontrolled mitosis.

During angiogenesis, endothelial cells proliferate, migrate into new tissue and form inter-endothelial junctions leading to tube formation. This process starts and is driven by angiogenic factors. The signalling of VEGFs and angiopoietins leads to loosening of the pericyte-endothelial contact permitting proliferation and interaction of new endothelial cells with the extracellular matrix mediated by integrins. The $\alpha v \beta 3$ and $\alpha v \beta 5$ integrins have been described to participate in blood vessel development and angiogenesis via a signalling crosstalk with angiogenic factors.

In addition to interactions between endothelial cells and the extra-cellular matrix, the regulation of inter-endothelial contacts is important for tube formation. For example, the adhesion molecule VE-cadherin plays a role in vascular remodelling and maintains integrity of blood vessels.

In the research that led to the present invention the junctional adhesion molecules (hereafter JAM) JAM-B and JAM-C were discovered. These molecules are found in vascular cell-cell contacts and are involved in leukocyte transendothelial migration. Now it was found that the interaction between JAM-B and JAM-C also plays an important role in angiogenesis.

SUMMARY OF THE INVENTION

The present invention is also directed to angiogenesis inhibiting molecules that are antibodies, antibody fragments, antibody derivatives or recombinant soluble proteins binding to JAM-B or JAM-C. The antibody fragments are selected from Fab fragments, Fv fragments, single domain antigen binding fragments, scFv and aggregates thereof, $V_{HH}s$.

The antibody derivatives are recombinant antibodies having the same specificity as the selected antibody, humanized derivatives of the selected antibody and chimeric antibodies based on the selected antibody.

The present invention is also directed to angiogenesis inhibiting molecules which are small molecules binding JAM-B or JAM-C. The present invention is also directed to angiogenesis inhibiting molecules selected from soluble JAM-B and soluble JAM-C.

As yet another aspect of the present invention is directed to an antibody that specifically binds mammalian JAM-Cs or JAM-Bs. The present invention is also directed to an anti-JAM-C or anti-JAM-B antibody that is a monoclonal antibody. The present invention is also directed to the antibody H33 which is produced by hybridoma 13H33 having the accession number DSM ACC2622. The present invention is also directed to an anti-JAM-C or anti-JAM-B antibody having one or more fragments selected from the group consisting of Fab fragments, Fv fragments, single domain antigen binding fragments, single domain antigen binding fragments, scFv and aggregates thereof of antibody H33. The present invention is also directed to an anti-JAM-C or anti-JAM-B antibody wherein the monoclonal antibodies are recombinant antibodies having the same specificity as antibody H33, humanized derivatives of antibody H33, and chimeric antibodies based on antibody H33.

The present invention is also directed to a composition for the treatment of carcinoma, in particular for the treatment of solid tumor carcinomas, comprising a therapeutically effective amount of one or more of the foregoing angiogenesis inhibiting molecules and an excipient, carrier or diluent.

The present invention is also directed to a preparation of compositions for the treatment of solid tumor carcinomas.

The present invention is also directed to a method for reducing angiogenesis from solid tumor cells comprising contacting the solid tumor cells with a mammalian anti-JAM-C and anti-JAM-B antibody. The present invention is also directed to a method for treating carcinomas, more particularly, solid tumor carcinomas, comprising contacting the mutant cancer cells with a mammalian anti-JAM-C or anti-JAM-B antibody and is used to treat solid tumor carcinomas (for example, but not limited to) breast, throat, brain, liver, kidney, stomach, pancreas, prostate, testes, ovaries, skin, lung, small and large intestine, colon, and bone.

As yet another aspect of the present invention is directed to a mammalian anti-JAM-C or anti-JAM-B antibody further comprising a therapeutic agent wherein the therapeutic agent is optionally bound to the antibody. The present invention is also directed to a mammalian anti-JAM-C or anti-JAM-B antibody wherein the therapeutic agent is selected from the group consisting of a radioisotope, a cytotoxin, an immunomodulatory agent, a chemotherapeutic agent, an anti-angiogenic agent, a therapeutic gene, a radioisotope, and detectable label. The present invention is also directed to an anti-JAM-C or anti-JAM-B antibody that is linked to a fluorescent molecule for use in magnetic resonance imaging, scintigraphic imaging, ultrasound, and fluorescence.

As yet another aspect of the present invention is directed to a mammalian anti-JAM-C or anti-JAM-B antibody comprising at least one light chain and at least one heavy chain, wherein one or both of the at least one light chain and at least one heavy chain comprise a variable region having mammalian residues and non-mammalian residues and a mammalian constant region and wherein the mammalian anti-JAN-C antibody binds to mammalian JAM-C antigen or JAMB antigen.

The present invention is also directed to a method for determining the presence of JAM-C or JAM-B in a biological sample comprising the steps of obtaining a biological sample, exposing said biological sample to a mammalian angiogenesis-inducing factor specific antibody; and detecting the binding of mammalian angiogenesis-inducing specific antibody in said biological sample.

The present invention provides methods for providing molecules that are capable of inhibiting angiogenesis, comprising the steps of:
a) providing a range of molecules;
b) testing whether these molecules can prevent interaction between JAM-B and JAM-C;
c) testing the positive molecules for their ability to block angiogenesis in vivo; and
d) selecting molecules that are positive in the angiogenesis test as angiogenesis inhibiting molecules.

The invention is also directed to use of the in vivo angiogenesis retina test in step c) of the method. The present invention is also directed to the further step of testing the positive molecules for their ability to inhibit tumor growth in vivo in addition to or instead of step c). The present invention is also directed to a test for inhibiting tumor growth in vivo.

As yet another aspect of the invention is directed to isolating or producing the angiogenesis inhibiting molecules. The present invention is also directed to the method wherein the range of molecules provided in step a) is a population of antibodies directed against JAM-B or JAM-C. The present invention is also directed to a method wherein the range of molecules provided in step a) is a population of small molecules binding to JAM-B or JAM-C. The present invention is also directed to the method wherein the small molecules are unnatural chemical compounds.

The present invention is also directed to a method for testing whether molecules are capable of inhibiting angiogenesis, wherein methods of testing whether molecules can prevent interaction between JAM-B and JAM-C is performed by contacting cells expressing either JAM-B or JAM-C on their surface with labelled soluble JAM-C or JAM-B, respectively, in the presence of the molecule to be tested to establish binding between JAM-B or JAM-C on the cell and the labelled soluble JAM-C or JAM-B or molecule to be tested for obtaining a population of labelled and/or unlabelled cells and visualizing the label, and wherein molecules that induce a decrease in the amount of label visualized in comparison to control cells expressing JAM-C or JAM-B and having labelled JAM-B or JAM-C but no molecule to be tested bound to their surface are selected as positive molecules. The present invention is also directed to testing whether molecules can prevent interaction between JAM-B and JAM-C by incubating cells expressing either JAM-B or JAM-C on their surface with labelled soluble JAM-C or JAN-B, respectively, in the presence of said molecules and recording a decrease in labelling of the cells as compared to control incubation without said molecules. Molecules that induce a decrease in the amount of label visualized in comparison to control cells expressing JAM-C or JAM-B and having labelled JAM-B or JAM-C but no molecule to be tested bound to their surface are selected as positive molecules.

As yet another aspect of the invention are the angiogenesis inhibiting molecules obtainable by the methods selected as positive in the angiogenesis test as angiogenesis inhibiting molecules.

Other aspects and advantages of the invention may be apparent to those skilled in the art from a review of the following detailed description, including any drawings, as well as approved claims.

DETAILED DESCRIPTION

Figure 1:
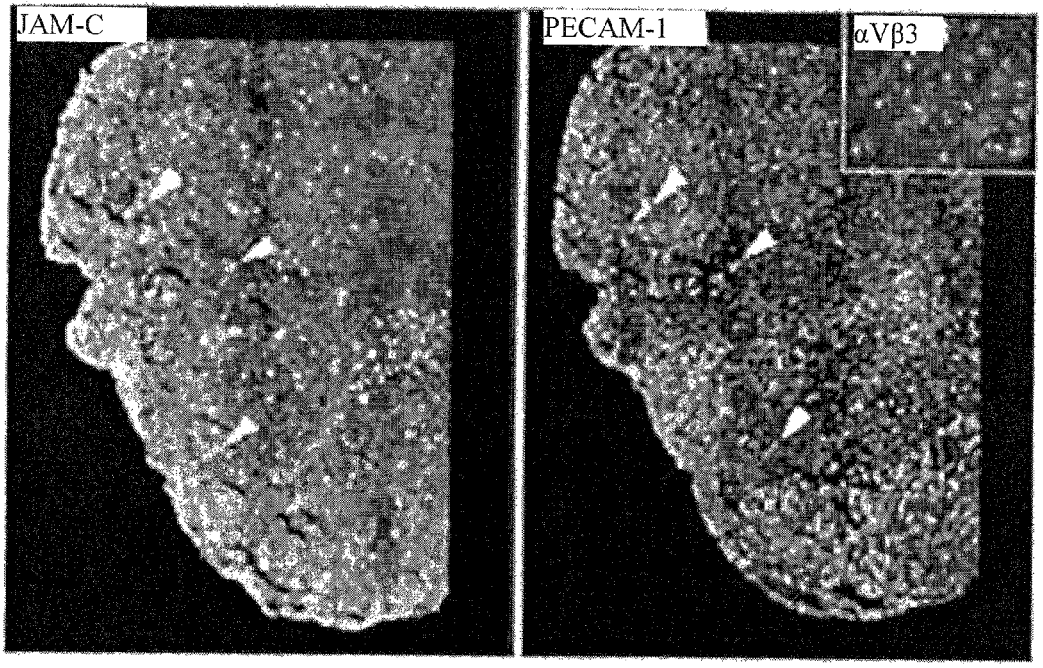
FIG. 1 demonstrates that JAM-C is expressed by blood vessels in human liver tumor. JAM-C expression was analysed with a panel of angiogenic tumors. The transcripts encoding human JAM-C are not present in normal liver. Immunostaining of frozen sections with anti-JAM-C antibody shows expression by a subpopulation of blood vessels (arrowheads). Staining with a polyclonal antibody against PECAM-1 to visualize vascular structures is shown on the right panel and the angiogenic characteristic of the tumor was controlled by V.3 staining (insert).

The present invention provides new molecules that are capable of inhibiting angiogenesis.

These molecules are provided by the present invention by a method, comprising the steps of:
a) providing a range of molecules;
b) testing whether these molecules can prevent interaction between JAM-B and JAM-C;
c) testing the positive molecules for their ability to block angiogenesis in vivo; and
d) selecting molecules that are positive in the in vivo test as angiogenesis inhibiting molecules.

Testing the molecules for their ability to block angiogenesis in vivo may be performed by means of the retina test as described in Example 4.

According to the invention it was found that not all molecules that can prevent the interaction between JAM-B and JAM-C are also capable of inhibiting angiogenesis. The additional test of step d) above is therefore necessary to find the desired molecules.

In another embodiment the invention may further comprise the step of testing the positive molecules for their ability to inhibit tumor growth in vivo. The test for inhibiting tumor growth in vivo is for example a test as described in Example 5.

The method of the invention may further comprise the step of isolating or producing the angiogenesis inhibiting molecules thus resulting in the actual obtainment of the desired molecules.

Selective Binding Agents

The range of molecules that can be tested according to the invention can be diverse. In a first embodiment, the range of molecules is a population of antibodies directed against JAM-B or JAM-C. The preparation of antibodies may be undertaken by the method of Köhler & Milstein, Nature 256: 495-497 (1975). Once the desired antibody is selected it can be produced by means of techniques set forth below.

The term "selective binding agent" refers to a molecule that binds either to JAM-B or JAM-C polypeptides. Suitable selective binding agents include, but are not limited to, antibodies and derivatives thereof, polypeptides, and small molecules. Suitable selective binding agents may be prepared using methods known in the art. An exemplary of JAM-C polypeptide selective binding agent of the present invention is capable of binding a certain portion of the JAM-C polypeptide thereby inhibiting interaction or binding to each other between JAM-B and JAM-C. An exemplary JAM-B polypeptide selective binding agent of the present invention is capable of binding a certain portion of the JAM-B polypeptide thereby inhibiting interaction or binding to each other between JAM-B and JAM-C. These "selective binding agents" or "small molecules" are also reviewed in Schreiber, S. L., Chem. & Eng. News 81: 51-61 (2003) and Ellman, Edgar Jacoby, John Davies and Marcel J. J. Bloomers, Current Topics in Medicinal Chemistry, Vol. 3, No. 1, 2003, pages 11-23.

The invention further relates to antibody fragments and antibody derivatives that retain the antigen binding capacity of the whole antibody. Functional antigen-binding antibody fragments can be engineered by proteolysis of antibodies (papain digestion, pepsin digestions or other enzymatic approaches), yielding Fab, Fv or single domains. Alternatively, fragments can be produced recombinantly. Fab fragments ("Fragment antigen binding") are the antigen-binding domains of an antibody molecule, containing $V_H$+$C_H1$ and $C_L$+$V_L$. Between $C_L$ and $C_H1$ an interchain disulfide bond is present. The molecular weight of the heterodimer is usually around 50 kDa. Fab fragments can be prepared by papain digestions of whole antibodies. The minimal fragment (~30 kDa) that still contains the whole antigen-binding site of a whole IgG antibody is composed of both the variable heavy chain ($V_H$) and variable light chain ($V_L$) domains. This heterodimer, called Fv fragment (for "Fragment variable") is still capable of binding the antigen. Another fragment is the single domain antigen binding fragment (dAbs) or $V_H$s. Single-chain Fv fragments can be made recombinantly. In the scFv fragment the $V_H$ and $V_L$ domains are joined with a hydrophilic and flexible peptide linker. scFvs can be complexed into dimers (diabodies), trimers (triabodies) or larger aggregates the monomeric units of which can have the same or different specificities. A further type of antibody fragment are the $V_{HH}$s comprising the smallest available intact antigen-binding fragment. $V_{HH}$s can be produced from proteolyses heavy chain antibodies of an immunised camelid or via recombinant techniques. Antibodies can furthermore be humanized and chimeric. These and other known or future antibody fragments or antibody derivatives having the ability to prevent the interaction between JAM-B and JAM-C and to inhibit angiogenesis in vivo are part of this invention. The production of antibody fragments and antibody fusion proteins is reviewed in Joosten, V. et al., *Microb Cell Fact.* 2(1): 1 (2003).

Selective binding agents such as antibodies and antibody fragments that bind either JAM-B or JAM-C polypeptides are within the scope of the present invention. The antibodies may be polyclonal including monospecific polyclonal; monoclonal (MAbs); recombinant; chimeric; humanized, such as complementarity-determining region (CDR)-grafted; human; single chain; and/or bispecific; as well as fragments; variants; or derivatives thereof. Antibody fragments include those portions of the antibody that bind to an epitope on the either JAM-B or JAM-C polypeptide. Examples of such fragments include Fab and F(ab') fragments generated by enzymatic cleavage of full-length antibodies. Other binding fragments include those generated by recombinant DNA techniques, such as the expression of recombinant plasmids containing nucleic acid sequences encoding antibody variable regions.

Polyclonal antibodies directed toward a either JAM-B or JAM-C polypeptide generally are produced in animals (e.g., rabbits or mice) by means of multiple subcutaneous or intraperitoneal injections of either JAM-B or JAM-C polypeptide and an adjuvant. It may be useful to conjugate a either JAM-B or JAM-C polypeptide to a carrier protein that is immunogenic in the species to be immunized, such as keyhole limpet hemocyanin, serum, albumin, bovine thyroglobulin, or soybean trypsin inhibitor. Also, aggregating agents such as alum are used to enhance the immune response. After immunization, the animals are bled and the serum is assayed for anti-either JAM-B or JAM-C antibody titer.

Monoclonal antibodies directed toward either JAM-B or JAM-C polypeptides are produced using any method that provides for the production of antibody molecules by continuous cell lines in culture. Examples of suitable methods for preparing monoclonal antibodies include the hybridoma methods of Köhler et al., 1975, Nature 256: 495-97 and the human B-cell hybridoma method (Kozbor, 1984, J. Immunol. 133: 3001; Brodeur et al., Monoclonal Antibody Production Techniques and Applications 51-63 (Marcel Dekker, Inc., 1987). Also provided by, the invention are hybridoma cell lines that produce monoclonal antibodies reactive with either JAM-B or JAM-C polypeptides.

Monoclonal antibodies of the invention may be modified for use as therapeutics. One embodiment is a "chimeric"

antibody in which a portion of the heavy (H) and/or light (L) chain is identical with or homologous to a corresponding sequence in antibodies derived from a particular species or belonging to a particular antibody class or subclass, while the remainder of the chain(s) is/are identical with or homologous to a corresponding sequence in antibodies derived from another species or belonging to another antibody class or subclass. Also included are fragments of such antibodies, so long as they exhibit the desired biological activity. See U.S. Pat. No. 4,816,567; Morrison et al., 1985, Proc. Natl. Acad. Sci. 81: 6851-55.

In another embodiment, a monoclonal antibody of the invention is a "humanized" antibody. Methods for humanizing non-human antibodies are well known in the art. See U.S. Pat. Nos. 5,585,089 and 5,693,762. Generally, a humanized antibody has one or more amino acid residues introduced into it from a source that is non-human. Humanization can be performed, for example, using methods described in the art (Jones et al., 1986, Nature 321: 522-25; Riechmann et al., 1998, Nature 332: 323-27; Verhoeyen et al., 1988, Science 239: 1534-36), by substituting at least a portion of a rodent complementarity-determining region for the corresponding regions of a human antibody.

Also encompassed by the invention are human antibodies that bind either JAM-B or JAM-C polypeptides. Using transgenic animals (e.g., mice) that are capable of producing a repertoire of human antibodies in the absence of endogenous immunoglobulin production such antibodies are produced by immunization with a either JAM-B or JAM-C polypeptide antigen (i.e., having at least 6 contiguous amino acids), optionally conjugated to a carrier. See, e.g., Jakobovits et al., 1993, Proc. Natl. Acad. Sci. 90: 2551-55; Jakobovits et al., 1993, Nature 362: 255-58; Bruggermann et al., 1993, Year in Immuno. 7:33. In one method, such transgenic animals are produced by incapacitating the endogenous loci encoding the heavy and light immunoglobulin chains therein, and inserting loci encoding human heavy and light chain proteins into the genome thereof. Partially modified animals, that is animals having less than the full complement of modifications, are then cross-bred to obtain an animal having all of the desired immune system modifications. When administered an immunogen, these transgenic animals produce antibodies with human (rather than, e.g., murine) amino acid sequences, including variable regions that are immunospecific for these antigens. See International Pub. Nos. WO 96/33735 and WO 94/02602. Additional methods are described in U.S. Pat. No. 5,545,807, International Pub. Nos. WO 91/10741 and WO 90/04036, and in European Patent Nos. 546073B1 and 546073A1. Human antibodies can also be produced by the expression of recombinant DNA in host cells or by expression in hybridoma cells as described herein.

In an alternative embodiment, human antibodies can also be produced from phage-display libraries (Hoogenboom et al., 1991, J. Mol. Biol. 227:381; Marks et al., 1991, J. Mol. Biol. 222:581). These processes mimic immune selection through the display of antibody repertoires on the surface of filamentous bacteriophage, and subsequent selection of phage by their binding to an antigen of choice. One such technique is described in International Pub. No. WO 99/10494, which describes the isolation of high affinity and functional agonistic antibodies for MPL- and msk-receptors using such an approach.

Chimeric, CDR grafted, and humanized antibodies are typically produced by recombinant methods. Nucleic acids encoding the antibodies are introduced into host cells and expressed using materials and procedures described herein. In a preferred embodiment, the antibodies are produced in mammalian host cells, such as CHO cells. Monoclonal (e.g., human) antibodies may be produced by the expression of recombinant DNA in host cells or by expression in hybridoma cells as described herein.

In a particular embodiment the invention relates to the monoclonal antibody H33, deposited with the Deutsch Sammlung von Mikroorganismen und Zellkulturen GmbH (DSM), Mascheroder Weg 1B, D-3300 Braunschweig, Germany under the Budapest Treaty on Oct. 22, 2003 under the deposit accession number DSM ACC2622. It was shown that antibody H33, which is directed against JAM-C, can block angiogenesis in vitro and in vivo and prevent tumor growth in vivo. It can also block the interaction of JAM-C with JAM-B.

The invention relates to the antibody H33 for use as a therapeutic agent, in particular for treatment of cancer, more in particular for treating solid tumors. In addition the invention relates to fragments and derivatives of H33, in particular Fab fragments, Fv fragments, single domain antigen binding fragments, recombinant antibodies having the specificity of H33, scFv and aggregates thereof, $V_{HH}s$, humanized derivatives of H33 and chimeric antibodies comprising at least the specificity of H33.

The anti-JAM-B or anti-JAM-C antibodies of the invention may be employed in any known assay method, such as competitive binding assays, direct and indirect sandwich assays, and immunoprecipitation assays (Sola, Monoclonal Antibodies: A Manual of Techniques 147-156 (CRC Press, Inc., 1987)) for the detection and quantitation of either JAM-B or JAM-C polypeptides. The antibodies will bind either JAM-B or JAM-C polypeptides with an affinity that is appropriate for the assay method being employed.

For diagnostic applications, in certain embodiments, anti-JAM-B or anti-JAM-C antibodies may be labeled with a detectable moiety. The detectable moiety can be any one that is capable of producing, either directly or indirectly, a detectable signal. For example, the detectable moiety may be a radioisotope, such as $^{18}$fluorine, $^{64}$copper, $^{65}$copper, $^{67}$gallium, $^{68}$gallium, $^{77}$bromine, $^{80m}$bromine, $^{95}$ruthenium, $^{97}$ruthenium, $^{103}$ruthenium, $^{105}$ruthenium, $^{99m}$technetium, $^{107}$mercury, $^{203}$mercury, $^{123}$iodine, $^{124}$iodine, $^{125}$iodine, $^{126}$iodine, $^{131}$iodine, $^{133}$iodine, $^{111}$rhenium, $^{113}$mindium, $^{99m}$rhenium, $^{105}$rhenium, $^{101}$rhenium, $^{186}$rhenium, $^{188}$rhenium, $^{121}$mtellurium, $^{99}$technetium, $^{122m}$mtellurium, $^{125m}$tellurium, $^{165}$thulium, $^{167}$thulium, $^{168}$thulium, $^{90}$yttrium, and nitride or oxide forms derived there from. Other suitable radioisotopes include alpha emitters, such as $^{213}$bismuth, $^{213}$lead, and $^{225}$actinium; a fluorescent or chemiluminescent compound, such as fluorescein isothiocyanate, rhodamine, or luciferin; or an enzyme, such as alkaline phosphatase, .beta.-galactosidase, or horseradish peroxidase (Bayer, et al., 1990, Meth. Enz. 184: 138-63).

Competitive binding assays rely on the ability of a labeled standard (e.g., a either JAM-B or JAM-C polypeptide, or an immunologically reactive portion thereof) to compete with the test sample analyte (either JAM-B or JAM-C polypeptide) for binding with a limited amount of anti-JAM-B or anti-JAM-C antibody. The amount of a either JAM-B or JAM-C polypeptide in the test sample is inversely proportional to the amount of standard that becomes bound to the antibodies. To facilitate determining the amount of standard that becomes bound, the antibodies typically are insolubilized before or after the competition, so that the standard and analyte that are bound to the antibodies may conveniently be separated from the standard and analyte that remain unbound.

Sandwich assays typically involve the use of two antibodies, each capable of binding to a different immunogenic portion, or epitope, of the protein to be detected and/or quantitated. In a sandwich assay, the test sample analyte is typically bound by a first antibody that is immobilized on a solid support, and thereafter a second, antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assays). For example, one type of sandwich assay is an enzyme-linked immunosorbent assay (ELISA), in which case the detectable moiety is an enzyme.

The selective binding agents, including anti-JAM-B or anti-JAM-C antibodies, are also useful for in vivo imaging. An antibody labeled with a detectable moiety may be administered to an animal, preferably into the bloodstream, and the presence and location of the labeled antibody in the host assayed. The antibody may be labeled with any moiety that is detectable in an animal, whether by nuclear magnetic resonance, radiology, or other detection means known in the art.

Selective binding agents of the invention, including antibodies, may be used as therapeutics. These therapeutic agents are generally agonists or antagonists, in that they either enhance or reduce, respectively, at least one of the biological activities of a either JAM-B or JAM-C polypeptide. In one embodiment, antagonist antibodies of the invention are antibodies or binding fragments thereof which are capable of specifically binding to a either JAM-B or JAM-C polypeptide and which are capable of inhibiting or eliminating the functional activity of a either JAM-B or JAM-C polypeptide in vivo or in vitro. In preferred embodiments, the selective binding agent, e.g., an antagonist antibody, will inhibit the functional activity of a either JAM-B or JAM-C polypeptide by at least about 50%, and preferably by at least about 80%. In another embodiment, the selective binding agent may be an anti-JAM-B or anti-JAM-C polypeptide antibody that is capable of interacting with a either JAM-B or JAM-C polypeptide binding partner (a ligand or receptor) thereby inhibiting or eliminating either JAM-B or JAM-C polypeptide activity in vitro or in vivo. Selective binding agents, including agonist and antagonist anti-JAM-B or anti-JAM-C polypeptide antibodies, are identified by screening assays that are well known in the art.

The invention also relates to a kit comprising either JAM-B or JAM-C selective binding agents (such as antibodies) and other reagents useful for detecting either JAM-B or JAM-C polypeptide levels in biological samples. Such reagents may include a detectable label, blocking serum, positive and negative control samples, and detection reagents.

Uses of Mammalian Anti-JAM-B or JAM-C Antibodies

In Vitro Applications

The present invention provides in vitro methods using mammalian anti-JAM-B or JAM-C antibodies. For example, the disclosed antibodies can be used to specifically bind JAM-C expressing cells. Specific binding of anti-JAM-C or JAM-B antibodies can be used for depleting a biological sample of JAM-C cells. Specific anti-JAM-C antibodies block neovascularization can be used for depleting a biological sample JAM-C expressing cells, for example, endothelial cells. Specific H-33 anti-JAM-C antibodies effect tumor angiogenesis and tumor growth. Also anti-JAM-C antibody is not toxic to mammals.

The term "carcinoma" is used in reference to a malignant growth of mutant cancer cells tending to infiltrate the surrounding tissue and give rise to metastases. Carcinomas may include cancerous cells which exhibit the properties of invasion and metastasis and are highly anaplastic. Carcinoma is synonymous with cancer. Solid tumor carcinoma is referenced as a swelling and morbid enlargement and/or new growth of tissue in which the multiplication of cancerous mutant cells is uncontrolled and progressive and is a neoplasm.

Detection Methods

Mammalian or humanized anti-JAM-B or anti-JAM-C antibodies of the invention also have utility in the detection of JAM-B or JAM-C expressing cells in vitro and in vivo based on their ability to specifically bind the JAM-B OR JAM-C antigen. A method for detecting JAM-B or JAM-C-expressing cells can comprise: (a) preparing a biological sample comprising cells; (b) contacting a humanized or mammalian anti-JAM-B or anti-JAM-C antibody with the biological sample in vitro, wherein the antibody comprises a detectable label; and (c) detecting the detectable label, whereby JAM-B or JAM-C-expressing cells are detected.

The disclosed detection methods can also be performed in vivo, for example as useful for diagnosis or for dose determination. Following administration of a labeled humanized or mammalian anti-JAM-B or anti-JAM-C antibody to a subject, and after a time sufficient for binding, the biodistribution of JAM-B OR JAM-C expressing cells bound by the antibody can be visualized. The term "time sufficient for binding" refers to a temporal duration that permits binding of the antibody to bind JAM-B OR JAM-C expressing cells in vivo.

The term "subject," as used in reference to in vivo diagnostic methods, and also used in reference to treatment methods described herein below, means any mammalian species. While the methods of the present invention are contemplated for the treatment of cancers in humans, the anti-JAM-B or anti-JAM-C antibodies of the invention may also have diagnostic and/or therapeutic value in preventing other angiogenesis diseases in mammals including humans.

In accordance with the present invention, the disclosed diagnostic methods can be used in combination with treatment methods, described herein below. In addition, humanized anti-JAM-B or anti-JAM-C antibodies of the invention can be administered for the dual purpose of detection and therapy.

Treatment Methods

The present invention further relates to methods and compositions useful for preventing angiogenesis in a subject, reduction of solid tumors in a subject, or to prevent vascularization of tumors by binding to JAM-B or JAM-C polypeptide. The term JAM-C or JAM-B depleting antibody or "anti-JAM-B or anti-JAM-C antibody" is used for an antibody that blocks angiogenesis in vitro and in vivo and prevents tumor growth in vivo. For example, sprouting of new blood vessels as reduced by at least 50% using anti-JAM-C antibodies is described in Example 6.

Also provided are methods for treatment of JAM-B or JAM-C-associated diseases and conditions, in part via the above-noted activities of a humanized anti-JAM-B or anti-JAM-C antibody.

The term "treatment" refers to both therapeutic and prophylactic measures. Those in need of treatment include those already afflicted with the disease or disorder as well as those in which the disease or disorder is to be prevented. The subject to be treated may have been diagnosed as having the disease or disorder or may be predisposed or susceptible to the disease. In particular, solid tumors can be reduced with treatment with mammalian anti-JAM-C antibodies. See Example 6.

For therapeutic regimens comprising administration of a humanized anti-JAM-B or anti-JAM-C antibody in combination with chemotherapy, the chemotherapeutic regimen can include a plurality of chemotherapeutic agents, including two or more of the above-noted agents. For example, useful chemotherapeutic regimens include CVP (cyclophosphamide, vincristine and prednisone), CHOP (CVP and doxorubicin), C-MOPP (cyclophosphamide, vincristine, prednisone and procarbazine), CAP-BOP (CHOP plus procarbazine and bleomycin), m-BACOD (CHOP plus methotrexate, bleomycin and leucovorin), ProMACE-MOPP (prednisone, methotrexate, doxorubicin, cyclophosphamide, etoposide and leucovorin plus standard MOPP), ProMACE-CytaBOM (prednisone, doxorubicin, cyclophosphamide, etoposide, cytarabine, bleomycin, vincristine, methotrexate and leucovorin) and MACOP-B (methotrexate, doxorubicin, cyclophosphamide, vincristine, fixed dose prednisone, bleomycin and leucovorin). CHOP has also been combined with bleomycin, methotrexate, procarbazine, nitrogen mustard, cytosine arabinoside and etoposide. Those skilled in the art are readily able to determine standard dosages and scheduling for each of these regimens.

Formulation, Dose, and Administration

A humanized or mammalian anti-JAM-B or anti-JAM-C antibody of the invention is readily prepared and formulated for safe and efficacious clinical use. Suitable formulations for administration to a subject include aqueous and non-aqueous sterile injection solutions which can contain anti-oxidants, buffers, bacteriostats, antibacterial and antifungal agents (e.g., parabens, chlorobutanol, phenol, ascorbic acid, an thimerosal), solutes that render the formulation isotonic with the bodily fluids of the intended recipient (e.g., sugars, salts, and polyalcohols), suspending agents and thickening agents. Suitable solvents include water, ethanol, polyol (e.g., glycerol, propylene glycol, and liquid polyethylene glycol), and mixtures thereof. The formulations can be presented in unit-dose or multi-dose containers, for example sealed ampoules and vials, and can be stored in a frozen or freeze-dried (lyophilized) condition requiring only the addition of sterile liquid carrier immediately prior to use for administration to a subject or for subsequent radiolabeling with an isotope appropriate for the intended application. Preparation of lyophilized formulations is described in PCT International Publication No. WO 97/04801. The formulations according to the invention are buffered to a pH of from about 5 to about 7, or about 6.

A representative anti-JAM-B or anti-JAM-C antibody formulation comprises a liquid multi-dose formulation of 40 mg/mL anti-JAM-B antibody or anti-JAM-C antibody, 25 mM acetate, 150 mM trehalose, 0.9% benzyl alcohol, 0.02% polysorbate 20 at pH 5.0, and which has a minimum shelf life of two years storage at 2-8° C. As another example, an anti-JAM-B or anti-JAM-C antibody formulation can comprise 10 mg/mL anti-JAM-B antibody or anti-JAM-C antibody in 9.0 mg/mL sodium chloride, 7.35 mg/mL sodium citrate dihydrate, 0.7 mg/mL polysorbate 80, and sterile water, pH6.5. See PCT International Publication No. WO 98/56418.

A humanized or mammalian anti-JAM-B or anti-JAM-C antibody can be administered parenterally, for example, via intravascular, subcutaneous, or intramuscular administration. For delivery of compositions to pulmonary pathways, compositions can be administered as an aerosol or coarse spray. Guidelines for administration of radiolabeled anti-JAM-B or anti-JAM-C antibodies can be found in Wagner et al. (2002) *J Nucl Med* 43: 267-72. For treatment of central nervous system (CNS) lymphomas, intrathecal administration can be used, as described by Rubenstein et al. (2003) *Blood* 101: 466-8. A delivery method is selected based on considerations such as the condition and site to be treated, the type of antibody formulation, and the therapeutic efficacy of the composition.

The present invention provides that an effective amount of a humanized or mammalian anti-JAM-B or anti-JAM-C antibody is administered to a subject. The term "effective amount" is used herein to describe an amount of a humanized or mammalian anti-JAM-B or anti-JAM-C antibody sufficient to elicit a desired biological response. For example, when administered to a cancer-bearing subject, an effective amount comprises an amount sufficient to elicit an anti-cancer activity, including cancer cell cytolysis, inhibition of cancer cell proliferation, induction of cancer cell apoptosis, reduction of cancer cell antigens, inhibition of cancer growth and metastasis, and/or induction of cancer resistance. An anti-JAM-B or anti-JAM-C antibody can be administered at a dosage of about 0.05 mg to about 100 mg per mg body weight per day, or about 0.5 mg to about 10 mg per kg body weight per day.

A radiolabeled anti-JAM-B or anti-JAM-C antibody can be administered at a dosage range from about 1 mCi to about 300 mCi, normally about 5 mCi to 100 mCi, depending on the radioisotope and the binding affinity of the antibody. Additional guidelines for therapeutic regimens employing a radiolabeled anti-JAM-B or anti-JAM-C antibody can be found in Behr et al. (1999) *Clin Cancer Res* 5: 3304s-3314s.

For methods comprising detection of JAM-B or JAM-C-positive expressing cells (i.e., tumor cells), a detectable amount of a composition of the invention is administered to a subject. A "detectable amount," as used herein to refer to a diagnostic composition, refers to a dose of a humanized anti-JAM-B or anti-JAM-C antibody such that the presence of the antibody can be determined in vitro or in vivo. For scintigraphic imaging using radioisotopes, typical doses of a radioisotope can include an activity of about 10 µCi to 50 mCi, or about 100 µCi to 25 mCi, or about 500 µCi to 20 mCi, or about 1 mCi to 10 mCi, or about 10 mCi.

Actual dosage levels of active ingredients in a composition of the invention can be varied so as to administer an amount of the composition that is effective to achieve the desired diagnostic or therapeutic outcome. Administration regimens can also be varied. A single injection or multiple injections can be used. The selected dosage level and regimen will depend upon a variety of factors including the activity of the therapeutic composition, formulation, the route of administration, combination with other drugs or treatments, the disease or disorder to be detected and/or treated, and the physical condition and prior medical history of the subject being treated. Determination and adjustment of an effective amount or dose, as well as evaluation of when and how to make such adjustments, are known to those of ordinary skill in the art of medicine. For example, typically a minimal dose is administered, and dose is escalated in the absence of dose-limiting toxicity.

For combination therapies, a humanized or mammalian anti-JAM-B or anti-JAM-C antibody and additional therapeutic or diagnostic agents are administered within any time frame suitable for performance of the intended therapy or diagnosis. Thus, the single agents can be administered substantially simultaneously (i.e., as a single formulation or within minutes or hours) or consecutively in any order. For example, single agent treatments can be administered within about 1 year of each other, such as within about 10, 8, 6, 4, or 2 months, or within 4, 3, 2 or 1 week(s), or within about 5, 4, 3, 2 or 1 day(s).

Measurable outcomes of the disclosed therapeutic methods vary according to the condition being treated and are readily determined by a skilled physician. For example, treatment of leukemia and lymphoma can be assessed by, inter alia, depletion of cancerous B cells. Recent reports describe the process of angiogenesis due to leukemia cancer cells in the bone marrow, Korkolopoulou, P. (2003) *Br. J. Haematol.*, 122: 900-910.

For additional guidance regarding formulation, dose, administration regimen, and measurable therapeutic outcomes, see Berkow et al. (2000) *The Merck Manual of Medical Information*, Merck & Co., Inc., Whitehouse Station, N.J.; Ebadi (1998) *CRC Desk Reference of Clinical Pharmacology*, CRC Press, Boca Raton, Fla.; Gennaro (2000) *Remington: The Science and Practice of Pharmacy*, Lippincott, Williams & Wilkins, Philadelphia, Pa.; Katzung (2001) *Basic & Clinical Pharmacology*, Lange Medical Books/McGraw-Hill Medical Pub. Div., New York; Hardman et al. (2001) *Goodman & Gilman's the Pharmacological Basis of Therapeutics*, The McGraw-Hill Companies, Columbus, Ohio; Speight & Holford (1997) *Avery's Drug Treatment: A Guide to the Properties, Choices, Therapeutic Use and Economic Value of Drugs in Disease Management*, Lippincott, Williams, & Wilkins, Philadelphia, Pa.

Preparation of Antibody Conjugates and Radiolabeled Antibodies

The present invention further provides antibody conjugates and radiolabeled antibodies comprising a humanized or mammalian anti-JAM-B or anti-JAM-C antibody of the invention. The conjugates and radiolabeled antibodies are useful in any of the methods described herein below.

The disclosed humanized or mammalian anti-JAM-B or anti-JAM-C antibodies are suitable for conjugation with any drug, either directly or indirectly. The term "drug" as used herein refers to any substance having biological or detectable activity. Thus, the term "drug" includes a pharmaceutical agent, a detectable label, a binding agent, etc.

The term "therapeutic agent" refers to any composition that can be used to treat or prevent a condition in a subject in need thereof. Representative therapeutic drugs include cytotoxins, radioisotopes, therapeutic genes, immunomodulatory agents, anti-angiogenic agents, chemotherapeutic agents, hormone regulators, and prodrugs. These drug descriptors are not mutually exclusive, and thus a therapeutic agent can be described using one or more of the above-noted terms. For example, selected radioisotopes are also cytotoxins. Therapeutic agents can be prepared as pharmaceutically acceptable salts, acids or derivatives of any of the above.

For radiotherapy applications, a humanized or mammalian anti-JAM-B or anti-JAM-C antibody of the invention can comprise a high energy radioisotope. The isotope can be directly bound to the antibody, for example, at a cysteine residue present in the antibody, or a chelator can be used to mediate the binding of the antibody and the radioisotope. Radioisotopes suitable for radiotherapy include but are not limited to β-emitters, γ-emitters, and auger electrons. Radioisotopes useful for diagnostic applications include but are not limited to positron emitters and β-emitters. A humanized or mammalian anti-JAM-B or anti-JAM-C antibody of the invention can further be iodinated, for example on a tyrosine residue of the antibody, to facilitate detection or therapeutic effect of the antibody.

Representative radioisotopes include $^{18}$fluorine, $^{64}$copper, $^{65}$copper, $^{67}$gallium, $^{68}$gallium, $^{77}$bromine, $^{80m}$bromine, $^{95}$ruthenium, $^{97}$ruthenium, $^{103}$ruthenium, $^{105}$ruthenium, $^{99m}$technetium, $^{107}$mercury, $^{203}$mercury, $^{123}$iodine, $^{124}$iodine, $^{125}$iodine, $^{126}$iodine, $^{131}$iodine, $^{133}$iodine, $^{111}$Indium, $^{113}$mindium, $^{99m}$rhenium, $^{105}$rhenium, $^{101}$rhenium, $^{186}$rhenium, $^{188}$rhenium, $^{121}$mtellurium, $^{99}$technetium, $^{122m}$tellurium, $^{125m}$tellurium, $^{165}$thulium, $^{167}$thulium, $^{168}$thulium, $^{90}$yttrium, and nitride or oxide forms derived there from. Other suitable radioisotopes include alpha emitters, such as $^{213}$bismuth, $^{213}$lead and $^{225}$actinium.

Methods for radioisotope-labeling of a molecule so as to be used in accordance with the disclosed methods are known in the art. For example, a targeting molecule can be derivatized so that a radioisotope can be bound directly to it (Yoo et al., J. Nucl. Med. 38: 294-300 (1997)). Alternatively, a linker can be added to enable conjugation. Representative linkers include diethylenetriamine pentaacetate (DTPA)-isothiocyanate, succinimidyl 6-hydrazinium nicotinate hydrochloride (SHNH), and hexamethylpropylene amine oxime (HMPAO) (Bakker et al., J. Nucl. Med. 31: 1501-1509 (1990); Chattopadhyay et al., Nucl. Med. Biol. 28: 741-744 (2001); Dewanjee et al., J. Nucl. Med. 35: 1054-1063 (1994); Krenning et al., Lancet 1: 242-244 (1989); Sagiuchi et al., Ann. Nucl. Med. 15: 267-270 (2001); U.S. Pat. No. 6,024,938). Iodination methods are also known in the art, and representative protocols can be found, for example, in Krenning et al. (1989) *Lancet* 1: 242-4 and in Bakker et al. (1990) *J Nucl Med* 31: 1501-9.

Angiogenesis and suppressed immune response play a central role in the pathogenesis of malignant disease and tumor growth, invasion, and metastasis. Thus, drugs useful in the methods of the present invention also include those able to induce an immune response and/or an anti-angiogenic response in vivo.

The term "immune response" is meant to refer to any response to an antigen or antigenic determinant by the immune system of a vertebrate subject. Exemplary immune responses include humoral immune responses (e.g. production of antigen-specific antibodies) and cell-mediated immune responses (e.g. lymphocyte proliferation).

Immunosuppressive agents include substances that suppress cytokine production, downregulate self-antigen expression, or mask MHC antigens. Representative immunosuppressive agents include 2-amino-6-aryl-5-substituted pyrimidines, azathioprine, cyclophosphamide, bromocryptine, danazol, dapsone, glutaraldehyde, anti-idiotypic antibodies for MHC antigens and MHC fragments, cyclosporin A, steroids such as glucocorticosteroids, cytokine or cytokine receptor antagonists (e.g., anti-interferon antibodies, anti-IL10 antibodies, anti-TNF antibodies, anti-IL2 antibodies), streptokinase, TGF, rapamycin, T-cell receptor, T-cell receptor fragments, and T cell receptor antibodies.

The term "angiogenesis" refers to the process by which new blood vessels are formed. The term "anti-angiogenic response" and "anti-angiogenic activity" as used herein, each refer to a biological process wherein the formation of new blood vessels is inhibited.

Representative chemotherapeutic agents include alkylating agents such as thiotepa and cyclosphosphamide; alkyl sulfonates such as busulfan, improsulfan and piposulfan; azidines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chiorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chiorczotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-EU; androgens such as calusterone, dromostanolone propionate, epitiostanol, mepitiostane, testolactone; anti-adrenal such as aminoglutethimide, mitotane, trilostane; folic acid replenisher such as frolinic acid; aceglatone; aldophosphamide glycoside; aminol evulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofuran; spirogermanium; tenuazonic acid; triaziquone; 2,2',2'-trichlorotriethylamine; urethan; vindesine; dacarbazine; mannomustine; mitobronitol; mitolactol; pipobroman; gacytosine; arabinoside ("Ara-C"); cylophosphamide; thiotepa; taxoids, e.g. paclitaxel (TAXOL®, Bristol-Myers Squibb Oncology of Princeton, N.J.) and doxetaxel (TAXOTERE®, Rhone-Poulenc Rorer of Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; and esperamicins; capecitabine.

The term "hormone regulators" refers to an agents that acts to regulate or inhibit hormone action on tumors such as anti-estrogens including for example tamoxifen, raloxifene, aromatase inhibiting 4 (5)-imidazoles, 4-hydroxytamoxifen, trioxifene, keoxifene, LY 117018, onapnstone, and toremifene; and anti-androgens such as flutamide, nilutamide, bicalutamide, leuprolide, and goserelin.

The term "prodrug" refers to a minimally cytotoxic precursor form of a therapeutic agent, which can be enzymatically activated or converted into a more active form. Representative prodrugs compatible with the invention include phosphate-containing prodrugs, thiophosphate-containing prodrugs, sulfate containing prodrugs, peptide containing prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs that can be converted to the more active cytotoxic free drug.

Additional therapeutic agents that can be conjugated to the humanized or mammalian anti-JAM-B or anti-JAM-C antibodies disclosed herein and used in accordance with the therapeutic methods of the present invention include but are not limited to alkylating agents such as melphalan and chlorambucil (Aboud-Pirak et al., Biochem. Pharmacol. 38: 641-648 (1989); Rowland et al., Cancer Immunol. Immunother. 37: 195-202 (1993)), vinca alkaloids such as vindesine and vinblastine (Aboud-Pirak et al., Biochem. Pharmacol. 38: 641-648 (1989); Starling et al., Bioconjug Chem. 3: 315-322 (1992)), antimetabolites such as 5-fluorouracil, 5-fluorouridine and derivatives thereof (Henn et al., J. Med. Chem. 36: 1570-1579 (1993); Krauer et al., Cancer Res. 52: 132-137 (1992)), photosensitizing agents (U.S. Patent Publication No. 2002/0197262 and U.S. Pat. No. 5,952,329) for photodynamic therapy, and magnetic particles for thermotherapy (U.S. Patent Publication No. 2003/0032995).

The term "binding agent" refers to a composition that specifically binds a target molecule. Representative binding agents include antibodies, targeting peptides, ligands, cell adhesion ligands, etc.

The term "detectable label" refers to a composition that can be detected following binding of a labeled antibody to antigen. For diagnostic methods using humanized or mammalian anti-JAM-B or anti-JAM-C antibodies, a drug can comprise a detectable label that can be used to detect the presence of JAM-B OR JAM-C expressing cells in vitro or in vivo. Radioisotopes useful for clinical diagnostic applications include labels that are detectable in vivo, such as those labels that are detectable using scintigraphy, magnetic resonance imaging, ultrasound, or fluorescence. Useful scintigraphic labels include positron emitters and β-emitters. Representative contrast agents for magnetic source imaging are paramagnetic or superparamagnetic ions (e.g., iron, copper, manganese, chromium, erbium, europium, dysprosium, holmium and gadolinium), iron oxide particles, and water soluble contrast agents. For ultrasonic detection, gases or liquids can be entrapped in porous inorganic particles that are released as microbubble contrast agents. For in vitro detection, useful detectable labels include a fluorophore, an epitope, or a radioactive label.

Selective Binding Agents

In a second embodiment the range of molecules is a population of selective binding agents which bind to JAM-B or JAM-C. Selective binding agents (molecular weight under 1,000 daltons) include but are not limited to sugars, amino acids, lipids, vitamins, hormones and chemicals. In the field of biotechnology "selective binding agent" is a well-understood term. In a preferred embodiment the small molecules are unnatural chemical compounds. Because the small molecules that are tested are already physically existent, the further step of producing the selected small molecule does not require inventive skill.

Testing whether selective binding agents can interrupt the interaction between JAM-B and JAM-C is for example performed by contacting cells expressing either JAM-B or JAM-C on their surface with labelled soluble JAM-C or JAM-B, respectively, in the presence of the selective binding agent to be tested to establish binding between JAM-B or JAM-C on the cell and the labelled soluble JAM-C or JAM-B or molecule to be tested for obtaining a population of labelled and/or unlabelled cells and visualizing the label, wherein selective binding agents that induce a decrease in the amount of label visualized in comparison to control cells expressing JAM-C or JAM-B and having labelled JAM-B or JAM-C but no molecule to be tested bound to their surface are selected as positive molecules.

Examples of suitable labels are fluorescent, radioactive or Biotin based labels. Suitable techniques for visualizing the label and disappearance or reduction thereof are flow cytometry, biochemistry, or enzyme linked immunosorbent assay (ELISA).

Selective binding agents that are found to inhibit the interaction between JAM-B and JAM-C are then further tested for their ability to inhibit angiogenesis in vivo. For this various options are available. However, the retina test as described in Example 5 is very well suited because the remodelling depends essentially on endothelial cells and not on microenvironmental factors. Alternative tests are the chorio allantois membrane assay, ischemic reperfusion, or angiogenesis induced by graft of matrigel loaded with angiogenic factors. These tests are well known in the art.

In addition to or instead, of testing the ability to inhibit angiogenesis in vivo, the capability of the molecule to inhibit tumor growth in vivo may be tested. A suitable example of such test is as described in Example 6.

The invention according to a further aspect thereof relates to angiogenesis inhibiting molecules (or selective binding agents) selected according to the method of claim 1 and subsequently produced. Such molecules may be antibodies or small molecules.

Chemically modified derivatives of either JAM-B or JAM-C selective binding agents may be prepared by one skilled in the art, given the disclosures described herein. Either JAM-B or JAM-C selective binding agents like JAM-B, JAM-C polypeptide derivatives are modified in a manner that is different—either in the type or location of the molecules naturally attached to the polypeptide. Derivatives may include molecules formed by the deletion of one or more naturally-attached chemical groups. Either JAM-B or JAM-C selective binding agents may be modified by the covalent attachment of one or more polymers. For example, the polymer selected is typically water-soluble so that the protein to which it is attached does not precipitate in an aqueous environment, such as a physiological environment. Included within the scope of suitable polymers is a mixture of polymers. Preferably, for therapeutic use of the end-product preparation, the polymer will be pharmaceutically acceptable.

The polymers each may be of any molecular weight and may be branched or unbranched. The polymers each typically have an average molecular weight of between about 2 kDa to about 100 kDa (the term "about" indicating that in preparations of a water-soluble polymer, some molecules will weigh more, some less, than the stated molecular weight). The average molecular weight of each polymer is preferably between about 5 kDa and about 50 kDa, more preferably between about 12 kDa and about 40 kDa and most preferably between about 20 kDa and about 35 kDa.

Suitable water-soluble polymers or mixtures thereof include, but are not limited to, N-linked or O-linked carbohydrates, sugars, phosphates, polyethylene glycol (PEG) (including the forms of PEG that have been used to derivatize proteins, including mono-($C_1$-$C_{10}$), alkoxy-, or aryloxy-polyethylene glycol), monomethoxy-polyethylene glycol, dextran (such as low molecular weight dextran of, for example, about 6 kD), cellulose, or other carbohydrate based polymers, poly-(N-vinyl pyrrolidone) polyethylene glycol, propylene glycol homopolymers, polypropylene oxide/ethylene oxide co-polymers, polyoxyethylated polyols (e.g., glycerol), and polyvinyl alcohol. Also encompassed by the present invention are bifunctional crosslinking molecules that may be used to prepare covalently attached either JAM-B or JAM-C polypeptide multimers.

In general, chemical derivatization may be performed under any suitable condition used to react a protein with an activated polymer molecule. For example, methods for preparing chemical derivatives of polypeptides or selective binding agents will generally comprise the steps of: (a) reacting the polypeptide with the activated polymer molecule (such as a reactive ester or aldehyde derivative of the polymer molecule) under conditions whereby the polypeptide comprising either JAM-B or JAM-C polypeptide, becomes attached to one or more polymer molecules, and (b) obtaining the reaction products. The optimal, reaction conditions will be determined based on known parameters and the desired result. For example, the larger the ratio of polymer molecules to protein, the greater the percentage of attached polymer molecule. In one embodiment, the either JAM-B or JAM-C polypeptide derivative may have a single polymer molecule moiety at the amino-terminus. See, e.g., U.S. Pat. No. 5,234,784.

The pegylation of a polypeptide may be specifically carried out using any of the pegylation reactions known in the art. Such reactions are described, for example, in the following references: Francis et al., 1992, Focus on Growth Factors 3: 4-10; European Patent Nos. 0154316 and 0401384; and U.S. Pat. No. 4,179,337. For example, pegylation may be carried out via an acylation reaction or an alkylation reaction with a reactive polyethylene glycol molecule (or an analogous reactive water-soluble polymer) as described herein. For the acylation reactions, a selected polymer should have a single reactive ester group. For reductive alkylation, a selected polymer should have a single reactive aldehyde group. A reactive aldehyde is, for example, polyethylene glycol propionaldehyde, which is water stable, or mono $C_1$-$C_{10}$ alkoxy or aryloxy derivatives thereof (see U.S. Pat. No. 5,252,714).

In another embodiment, either JAM-B or JAM-C selective binding agents may be chemically coupled to biotin. The biotin/either JAM-B or JAM-C selective binding agents are then allowed to bind to avidin, resulting in tetravalent avidin/biotin/either JAM-B or JAM-C selective binding agents. Either JAM-B or JAM-C selective binding agents may also be covalently coupled to dinitrophenol (DNP) or trinitrophenol (TNP) and the resulting conjugates precipitated with anti-DNP or anti-TNP-IgM to form decameric conjugates with a valency of 10.

In another embodiment, selective binding agents can be developed by chemical and biological methods which are well known in the art. For example, the generation of large combinational libraries of peptides and oligonucleotides can be screened against a receptor or enzyme to identify high-affinity ligands or potent inhibitors. For example libraries can be generated on solid supports of discrete compounds, split synthesis, deconvolution of soluble libraries, structural determination by analytical methods, encoding strategies. Synthesis of organic compound libraries can be generated using solid supports, post-synthesis peptide modification, biopolymer-mimetic libraries, nonoligomeric compound libraries, molecular recognition in designed receptor systems, and other analytical techniques. Libraries can also be synthesized in solution through spatially separate synthesis, or synthesis in pools of amides and esters, acetylcholinesterase inhibitors, amides displayed from a core molecule, or oligosaccharide libraries. Additional synthesis and application of small molecule libraries is discussed in Thompson et al., Chemical Reviews 96: 555-600 (1996), Jacoby et al., Current Topics in Medicinal Chemistry 3: 11-23 (2003), and Schreiber, S. L., Chem. & Eng. News 81: 51-61 (2003).

Generally, conditions that may be alleviated or modulated by the administration of the present either JAM-B or JAM-C selective binding agents include those described herein for either JAM-B or JAM-C selective binding agents. However, the JAM-B or JAM-C selective binding agents disclosed herein may have additional activities, enhanced or reduced biological activity, or other characteristics, such as increased or decreased half-life, as compared to the non-derivatized molecules.

Compositions

According to another embodiment the invention relates to the use of soluble JAM-B or JAM-C as a medicament, in particular for treatment of carcinomas, more in particular for treating solid tumor carcinomas.

The invention also relates to the use of the angiogenesis inhibiting molecules, such as H33, fragments and derivatives thereof, or soluble JAM-C or JAM-B for the preparation of a therapeutical composition for the treatment of cancer, in particular solid tumors.

Therapeutic compositions are within the scope of the present invention. Either JAM-B or JAM-C polypeptide pharmaceutical compositions may comprise a therapeutically effective amount of either anti-JAM-B or JAM-C polypeptide antibody in admixture with a pharmaceutically or physiologically acceptable formulation agent selected for suitability with the mode of administration. Pharmaceutical compositions may also comprise a therapeutically effective amount of one or more either JAM-B or JAM-C polypeptide selective binding agents in admixture with a pharmaceutically or physiologically acceptable formulation agent selected for suitability with the mode of administration.

Acceptable formulation materials preferably are nontoxic to recipients at the dosages and concentrations employed.

The pharmaceutical composition may contain formulation materials for modifying, maintaining, or preserving, for example, the pH, osmolarity, viscosity, clarity, color, isotonicity, odor, sterility, stability, rate of dissolution or release, adsorption, or penetration of the composition. Suitable formulation materials include, but are not limited to, amino acids (such as glycine, glutamine, asparagine, arginine, or lysine), antimicrobials, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; tromethamine; lecithin; cholesterol or tyloxapal), stability enhancing agents (such as sucrose or sorbitol), tonicity enhancing agents (such as alkali metal halides—preferably sodium or potassium chloride—or mannitol sorbitol), delivery vehicles, diluents, excipients and/or pharmaceutical adjuvants. See Remington's Pharmaceutical Sciences (18th Ed., A. R. Gennaro, ed., Mack Publishing Company 1990.

The optimal pharmaceutical composition will be determined by a skilled artisan depending upon, for example, the intended route of administration, delivery format, and desired dosage. See, e.g., Remington's Pharmaceutical Sciences, supra. Such compositions may influence the physical state, stability, rate of in vivo release, and rate of in vivo clearance of the either JAM-B or JAM-C molecule.

The primary vehicle or carrier in a pharmaceutical composition may be either aqueous or non-aqueous in nature. For example, a suitable vehicle or carrier for injection may be water, physiological saline solution, or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which may further include sorbitol or a suitable substitute. In one embodiment of the present invention, either JAM-B or JAM-C polypeptide compositions may be prepared for storage by mixing the selected composition having the desired degree of purity with optional formulation agents (Remington's Pharmaceutical Sciences, supra) in the form of a lyophilized cake or an aqueous solution. Further, either JAM-B or JAM-C polypeptide product may be formulated as a lyophilizate using appropriate excipients such as sucrose.

Either JAM-B or JAM-C polypeptide pharmaceutical compositions can be selected for parenteral delivery. Alternatively, the compositions may be selected for inhalation or for delivery through the digestive tract, such as orally. The preparation of such pharmaceutically acceptable compositions is within the skill of the art.

The formulation components are present in concentrations that are acceptable to the site of administration. For example, buffers are used to maintain the composition at physiological pH or at a slightly lower pH, typically within a pH range of from about 5 to about 8.

When parenteral administration is contemplated, the therapeutic compositions for use in this invention may be in the form of a pyrogen-free, parenterally acceptable, aqueous solution comprising the desired either JAM-B or JAM-C molecule in a pharmaceutically acceptable vehicle. A particularly suitable vehicle for parenteral injection is sterile distilled water in which a either JAM-B or JAM-C molecule is formulated as a sterile isotonic solution, properly preserved. Yet another preparation can involve the formulation of the desired molecule with an agent, such as injectable microspheres, bio-erodible particles, polymeric compounds (such as polylactic acid or, polyglycolic acid), beads, or liposomes, that provides for the controlled or sustained release of the product which may then be delivered via a depot injection. Hyaluronic acid may also be used, and this may have the effect of promoting sustained duration in the circulation. Other suitable means for the introduction of the desired molecule include implantable drug delivery devices.

In one embodiment, a pharmaceutical composition may be formulated for inhalation. For example, either JAM-B or JAM-C polypeptide may be formulated as a dry powder for inhalation. Either JAM-B or JAM-C polypeptide or nucleic acid molecule inhalation solutions may also be formulated with a propellant for aerosol delivery. In yet another embodiment, solutions may be nebulized. Pulmonary administration is further described in International Pub. No. WO 94/20069, which describes the pulmonary delivery of chemically modified proteins.

It is also contemplated that certain formulations may be administered orally. In one embodiment of the present invention, either selective binding agents of JAM-B or JAM-C polypeptides that are administered in this fashion can be formulated with or without those carriers customarily used in the compounding of solid dosage forms such as tablets and capsules. For example, a capsule may be designed to release the active portion of the formulation at the point in the gastrointestinal tract when bioavailability is maximized and presystemic degradation is minimized. Additional agents can be included to facilitate absorption of the either JAM-B or JAM-C polypeptide. Diluents, flavorings, low melting point waxes, vegetable oils, lubricants, suspending agents, tablet disintegrating agents, and binders may also be employed.

Another pharmaceutical composition may involve an effective quantity of either selective binding agents of anti-JAM-B or JAM-C polypeptides in a mixture with non-toxic excipients that are suitable for the manufacture of tablets. By dissolving the tablets in sterile water, or another appropriate vehicle, solutions can be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional either selective binding agents of anti-JAM-B or JAM-C polypeptide pharmaceutical compositions will be evident to those skilled in the art, including formulations involving either JAM-B or JAM-C polypeptides in sustained- or controlled-delivery formulations. Techniques for formulating a variety of other sustained- or controlled-delivery means, such as liposome carriers, bio-erodible microparticles or porous beads and depot injections, are also known to those skilled in the art. See, e.g., International Pub. No. WO 93/15722, which describes the controlled release of porous polymeric microparticles for the delivery of pharmaceutical compositions.

Additional examples of sustained-release preparations include semipermeable polymer matrices in the form of shaped articles, e.g. films, or microcapsules. Sustained release matrices may include polyesters, hydrogels, polylactides (U.S. Pat. No. 3,773,919 and European Patent No. 058481), copolymers of L-glutamic acid and gamma ethyl-L-glutamate (Sidman et al., 1983, Biopolymers 22: 547-56), poly(2-hydroxyethyl-methacrylate) (Langer et al., 1981, J. Biomed. Mater. Res. 15: 167-277 and Langer, 1982, Chem. Tech. 12: 98-105), ethylene vinyl acetate (Langer et al., supra) or poly-D(−)-3-hydroxybutyric acid (European Patent No. 133988). Sustained-release compositions may also include liposomes, which can be prepared by any of several methods known in the art. See, e.g., Eppstein et al., 1985, Proc. Natl. Acad. Sci. USA 82: 3688-92; and European Patent Nos. 036676, 088046, and 143949.

Either selective binding agents of JAM-E or JAM-C pharmaceutical composition to be used for in vivo administration typically must be sterile. This may be accomplished by filtration through sterile filtration membranes. Where the composition is lyophilized, sterilization using this method may be conducted either prior to, or following, lyophilization and reconstitution. The composition for parenteral administration may be stored in lyophilized form or in a solution. In addition, parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or as a dehydrated or lyophilized powder. Such formulations may be stored either in a ready-to-use form or in a form (e.g., lyophilized) requiring reconstitution prior to administration.

In a specific embodiment, the present invention is directed to kits for producing a single-dose administration unit. The kits may each contain both a first container having a dried protein and a second container having an aqueous formulation. Also included within the scope of this invention are kits containing single and multi-chambered pre-filled syringes (e.g., liquid syringes and lyosyringes).

The effective amount of either selective binding agents of JAM-B or JAM-C pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the either selective binding agents of JAM-B or JAM-C molecule is being used, the route of administration, and the size (body weight, body surface, or organ size) and condition (the age and general health) of the patient. Accordingly, the clinician may titer the dosage and modify the route of administration to obtain the optimal therapeutic effect. A typical dosage may range from about 0.1 µg/kg to up to about 100 mg/kg or more, depending on the factors mentioned above. In other embodiments, the dosage may range from 0.1 µg/kg up to about 100 mg/kg; or 1 µg/kg up to about 100 mg/kg; or 5 µg/kg up to about 100 mg/kg.

The frequency of dosing will depend upon the pharmacokinetic parameters of the either selective binding agents of JAM-B or JAM-C molecule in the formulation being used. Typically, a clinician will administer the composition until a dosage is reached that achieves the desired effect. The composition may therefore be administered as a single dose, as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages may be ascertained through use of appropriate dose-response data.

The route of administration of the pharmaceutical composition is in accord with known methods, e.g., orally; through injection by intravenous, intraperitoneal, intracerebral (intraparenchymal), intracerebroventricular, intramuscular, intraocular, intraarterial, intraportal, or intralesional routes; by sustained release systems; or by implantation devices. Where desired, the compositions may be administered by bolus injection or continuously by infusion, or by implantation device.

Alternatively or additionally, the composition may be administered locally via implantation of a membrane, sponge, or other appropriate material onto which the desired molecule has been absorbed or encapsulated. Where an implantation device is used, the device may be implanted into any suitable tissue or organ, and delivery of the desired molecule may be via diffusion, timed-release bolus, or continuous administration.

In some cases, it may be desirable to use either selective binding agents of JAM-B or JAM-C polypeptide pharmaceutical compositions in an ex vivo manner. In such instances, cells, tissues, or organs that have been removed from the patient are exposed to either JAM-B or JAM-C polypeptide pharmaceutical compositions after which the cells, tissues, or organs are subsequently implanted back into the patient.

In other cases, either selective binding agents of JAM-B or JAM-C polypeptide can be delivered by implanting certain cells that have been genetically engineered, using methods such as those described herein, to express and secrete the selective binding agents of either JAM-B or JAM-C polypeptide. Such cells may be animal or human cells, and may be autologous, heterologous, or xenogeneic. Optionally, the cells may be immortalized. In order to decrease the chance of an immunological response, the cells may be encapsulated to avoid infiltration of surrounding tissues. The encapsulation materials are typically biocompatible, semi-permeable polymeric enclosures or membranes that allow the release of the protein product(s) but prevent the destruction of the cells by the patient's immune system or by other detrimental factors from the surrounding tissues.

Therapeutic Uses

The invention also relates to therapeutical compositions for the treatment of carcinomas, in particular solid tumor carcinomas, comprising a therapeutically effective amount of one or more angiogenesis inhibiting molecules of the invention and a suitable excipient, carrier, diluent or other additive. The skilled person in the field of cancer therapy will be able to establish the therapeutically effective amount.

Either JAM-B or JAM-C nucleic acid molecules, polypeptides, and agonists and antibodies and antagonists thereof can be used to treat, diagnose, ameliorate, or prevent a number of diseases, disorders, or conditions, including those recited herein.

Either JAM-B or JAM-C polypeptide agonists, antibodies and antagonists include those molecules which inhibit the interaction between JAM-B and JAM-C polypeptides thus inhibiting angiogenesis. Agonists or antagonists may be co-factors, such as a protein, peptide, carbohydrate, lipid, or small molecular weight molecule, which interact with either JAM-B or JAM-C polypeptide and thereby regulate their interaction. Potential polypeptide agonists or antagonists include antibodies that react with either soluble or membrane-bound forms of either JAM-B or JAM-C polypeptides that comprise part or all of the extracellular domains of the said proteins.

Other antagonists or agonist s include those molecules that regulate either JAM-B or JAN-C polypeptide expression typically include nucleic acids encoding either JAM-B polypeptide that can act as anti-sense regulators of expression.

Since either JAM-B or JAM-C polypeptide expression has been detected in the lung, either JAM-B or JAM-C nucleic acid molecules, polypeptides, agonists and antagonists thereof (including, but not limited to, anti-either JAM-B or JAM-C selective binding agents) may be useful for the treatment or diagnosis of diseases involving solid tumors (e.g. carcinoma).

Expression of JAM-C has been detected in solid tumors of human liver where JAM-C is not present in normal liver tissue cells (Johnson-Leger C., Blood 100: 2479-2486 2002)). Therefore, dither JAM-B or JAM-C polypeptides play a role in the regulation of angiogenesis in primary and metastatic tumors. Accordingly, either JAM-B or JAM-C nucleic acid molecules, polypeptides, agonists and antagonists thereof (including, but not limited to, anti-either JAM-B or anti-JAM-C selective binding agents) may be useful as surrogate markers for the treatment or diagnosis of cancer diseases. Examples of such diseases include, but are not limited to, treating solid tumors (e.g., carcinoma) of breast cancer, throat cancer, brain cancer, liver cancer, kidney cancer, stomach cancer, pancreatic cancer, prostate cancer, testicular cancer, cancer of the ovaries, skin cancer, lung cancer, small and large intestine, colorectal cancer, and bone cancer. Other primary and metastatic cancer diseases are encompassed within the scope of the invention including, but not limited to acinar carcinoma, adenocystic carcinoma, adenoid cystic carcinoma, adenoid squamous carcinoma, adnexal carcinoma, aldosterone producing carcinoma, alveolar carcinoma, ameloblastic carcinoma, anaplastic carcinoma, apocrine carcinoma, basal cell (all types) carcinoma, bile duct carcinoma, bronchioalveolar carcinoma, cerebriform carcinoma, cholangiocellular carcinoma, chorionic carcinoma, choroid plexus carcinoma, colloid carcinoma, comedo carcinoma, corpus carcinoma, cortisol producing carcinoma, cribriform carcinoma, duct carcinomas, follicular carcinoma gastric, hepatocellular carcinoma, lymphoepithelial (any type) carcinoma, medullary carcinoma, meningeal carcinoma, mucoepidermoid carcinoma, nasopharyngeal carcinoma, renal cell carcinoma, scar carcinoma, schistosomal bladder carcinoma, scirrhous carcinoma, sebaceous carcinoma, terminal duct carcinoma, uterine corpus carcinoma, and verrucous carcinoma.

Agonists or antagonists of either JAM-B or JAM-C polypeptide function may be used (simultaneously or sequentially) in combination with one or more cytokines, growth factors, antibiotics, anti-inflammatories, and/or chemotherapeutic agents as is appropriate for the condition being treated.

Other diseases or disorders caused by or mediated by undesirable levels of either JAM-B or JAM-C polypeptides are encompassed within the scope of the invention. Undesirable levels include excessive levels of either JAM-B or JAM-C polypeptides and sub-normal levels of either JAM-B or JAM-C polypeptides.

The following Examples illustrate the methods of the invention with respect to providing molecules that are capable of inhibiting angiogenesis and the use of such methods in the inhibition of angiogenesis and tumor growth. Numerous improvements and further aspects of the invention are apparent to the skilled artisan upon consideration of the examples which follow.

EXAMPLES

Example 1

Preparation of a Population of Antibodies Against Jam-B or JAM-C

The present method was used in studies to establish a population of antibodies to be tested in the method of the invention is prepared according to Köhler & Milstein, Nature 256: 435-497 (1975). The source of antigen to obtain such population of antibodies consist in recombinant soluble JAM-B or JAM-C prepared as described in Example 3.

Example 2

Preparation of Soluble Jam-B and Jam-C

It was found by the present inventors that JAM-C interacts heterophilically with JAM-B through its V domain and that the soluble JAM-C V domain is sufficient for binding to JAM-B.

The soluble JAM-B and the soluble JAM-C V domain were obtained by PCR using the same cloning strategy. Primers were obtained from Microsynth (Microsynth GmbH, Balgach, Switzerland), and restriction sites added for cloning strategy are underlined. The cDNA encoding the extracellular V domain of JAM-C was amplified using plasmid encoding the full length sequence of murine JAM-C, Pfu polymerase, T7 and (5'-gctctagacagtgttgccgtcttgcctacag-3') (SEQ ID NO: 1) as forward and reverse primers. The PCR product-was digested with Hind III and XbaI before cloning in pcDNA3 containing FLAG-tag sequence.

The soluble JAM-B is prepared as follows: The cDNA encoding soluble JAM-B was obtained by PCR using (5'-tcagctaggcagccagct-3') (SEQ ID NO: 2) and (5'-gctctagaatctacttgcattcgcttcc-3') (SEQ ID NO:3) as forward and reverse primers. The PCR product, digested with XbaI was then cloned in frame with the FLAG Tag sequence in pcDNA3 using EcoRI/blunt and XbaI sites.

Example 3

Test for the Ability to Prevent Interaction Between JAM-B and JAM-C

Cells expressing either JAM-B or JAM-C on their surface are obtained by stable transfection of cells with vectors containing the sequence encoding JAM-B or JAM-C as described by Aurrand-Lions et al., J Biol Chem 276: 2733-41 (2001a); Aurrand-Lions et al., Blood 98: 3699-707 (2001b); Johnson-Leger et al., Blood 100: 2479-2486 (2002).

Soluble JAM-B and JAM-C obtained as described in Example 3 are labelled with sulfosuccinimidyl esters of Alexa 488
(Molecular Probes Inc.) or sulfo-NHS-Biotin (Pierce) according to the manufacturers procedures.

The cells expressing JAM-B or JAM-C are contacted with the labelled soluble JAM-C or JAM-B, respectively, in the presence of the molecules to be tested. The fluorescence is monitored with flow cytometry and decrease in fluorescence intensity as compared to the non treated control, indicates a decreased binding of soluble JAM-C or soluble JAM-B.

Example 4

Test for the Ability to Block Angiogenesis In Vivo

Postnatal day 7 (P7) mice are placed in 75% oxygen for five days causing central avascularization of retinas (Reynolds et al., Nature Medicine 8: 27-34 (2002)). This incubation is followed by housing the mice for five further days (until P17) under normoxic conditions. Mice are injected intraperitoneally with 50 mg of monoclonal antibodies at P12, P14 and P16. Neovascularization is detected by perfusion of the entire vasculature with a non-diffusible fluorescein-dextran solution. In flat-mounted retinas, areas of neovascularization and vascular glomeruli are detected. Vascular glomeruli are highly proliferative clusters of tortuous vessels that are produced in response to angiogenic stimuli and protrude through the inner limiting membrane. The numbers of glomeruli is counted to compare retinal neovascularization in mice treated with a molecule to be tested and in control mice.

One of the molecules tested is monoclonal antibody H33 which caused a reduction in neovascularization.

Example 5

Monoclonal Antibody H33 Directed Against Jam-C is an Inhibitor of Angiogenesis and Tumor Growth In order to demonstrate that antibody H33 against JAM-C block angiogenesis in vitro and prevent tumor growth in vivo, rat monoclonal antibodies (CRAM) against human and mouse JAM-C(H33, H36 and D33) and rat monoclonal antibodies against mouse PECAM-1/CD31 (GC51) and Lselectin/CD62L (Mel14) were previously described (Aurrand-Lions et al., 2001a, supra; Gallatin et al., Nature 330: 30-34 (1983); Piali et al., Eur J Immunol. 23: 2464-71 (1993); Springer et al., Eur. J. Immunol. 9: 301 (1979). Anti-human CD44 (9B5) used as irrelevant antibody control rat IgG2a was kindly provided by Dr B. Engelhardt (Laschinger and Engelhardt, 2000). Any other unrelated antibody can be used as a negative control. Polyclonal antibody against human JAM-B was prepared according to Palmeri et al., J Biol. Chem. 275: 19139-45 (2000). Monoclonal mouse anti-human integrin αvβ3 (LM609) were from Chemicon (Temecula, Calif.).

Endothelial Cells

Human Umbilical Vein Endothelial Cells (HUVEC) were isolated by collagenase treatment of umbilical veins (Wall R T et al., J Cell Physiol. 96: 203-213 (1978). HUVECs were maintained in M199 supplemented with 20% Fetal Calf Serum (PAA Laboratories), 25 mM HEPES (N-2-hydroxy-ethylpiperazine-N'-2-ethanesulfonic acid), nonessential amino acids, sodium pyruvate, endothelial cell growth supplement (ECGS, 15 µg/mL; Upstate Biotechnology, Lake Placid, N.Y.), and heparin (4 µg/ml; Sigma, Bucks, Switzerland). Cells were used between passages 3 and 5.

VEGF Stimulation $1.10^5$ HUVECs were plated on Growth Factor Reduced Matrigel (Becton Dickinson, Bedford, Mass., USA). After 48 hours, cells were incubated with 100 ng/ml recombinant human VEGF-165 (PeproTech House, London UK) for 15 minutes (immunocytochemistry) or 15 minutes to 24 hours (Flow cytometry).

Flow Cytometry

HUVECs were incubated with H36 anti-JAM-C monoclonal antibody on ice. After washing with PBS, BSA 0.2% binding of H36 antibody was detected using a phycoerythrin-coupled anti-rat antibody (Jackson Immunoresearch Laboratories, Inc., West Grove, Pa., USA). As control, the primary antibody was omitted. Analysis was performed using FACS-Calibur and Cellquest Software (Becton Dickinson, Mountain View, Calif., USA).

Immunostaining

For immunohistochemistry with monoclonal antibody anti-JAM-C(H36) and polyclonal antibody against JAM-B/VE-JAM, frozen sections were fixed with acetone/methanol 1:1 for 5 minutes at −20° C., dried and rehydrated in PBS, Gelatin 0.2%, Tween 20 0.05%. For immunocytochemistry, cells were fixed with paraformaldehyde 4% in PBS for 15 min prior permeabilization with TritonX100 0.01% in PBS for 10 min. Cells were washed with PBS, BSA 0.2%, incubated with primary antibodies for one hour and washed, before further incubation with secondary antibodies coupled to Texas Red, FITC or peroxidase (Jackson Immunoresearch Laboratories, Inc., West Grove, Pa., USA). Pictures were acquired using confocal microscope Zeiss LSM510. Glomerulonephritis was detected by kidney staining with periodic acid-Schiff (PAS).

Ex Vivo Aortic Ring Assay

Mouse aortic ring assays were performed as described (Nicosia, R. F. & Ottinetti, In Vitro Cell Dev Biol. 26(2):119-28 (1990). Briefly, 1-mm thoracic aortic rings were placed between two layers of 50 µl growth factor-reduced Matrigel (Becton Dickinson, Bedford, Mass., USA) optionally containing an antibody to be tested, and overlaid with 100 µl of DMEM supplemented with 20 U/ml heparin (Sigma-Aldrich corporation, Saint-Louis, Mo., USA) and ECGS (Upstate biotechnology, Lake Placid, N.Y., USA). Microvessel outgrowth was visualized by phase microscopy using a Zeiss Axioskop microscope.

Tumor Graft

Female 8- to 10-week-old C56BL6/J mice (Charles River laboratories, L'Arbresle, France) were inoculated subcutaneously with $1 \times 10^6$ murine Lewis lung carcinoma cells (LLC1). Mice were then injected intraperitoneally every second day with 150 µg of monoclonal antibody H33, isotype matched control antibody Me114 or PBS. When the control tumors (PBS injected mice) had reached 1-1.5 cm³ animals were sacrificed and tumors were excised and analysed.

Vessels Quantification

Tumor cryosections were stained with monoclonal anti-PECAM-1 antibody as described in Immunostaining Chapter. Pictures of the entire cryosections (4 cryosections per tumor) were taken using a Zeiss Axioskop microscope. PECAM-1 staining and the total area of the tumor were quantified using Zeiss KS400 software.

Evans Blue Permeability Assay

150 μg of anti-JAM-C or isotype-matched control antibodies were injected into the retro-orbital vein of anaesthetized mice. After 15 minutes, 100 μl of a 30 mg/kg Evans blue dye (Sigma-Aldrich corporation, Saint-Louis, Mo., USA) solution in saline was injected in the same way as antibodies, and circulated for one hour. Mice were then perfused with citrate-buffered 1% paraformaldehyde, pH 4.2, 37° C. to clear the dye out of the vessel lumina. Immediately after perfusion, the organs (kidney, lung, heart and brain) were dissected. After drying (Speed-Vac) of the tissue, the dried weight was measured. Evans blue was extracted by subsequent incubation of the tissue in 500 μl of formamide for 18 hours at 70° C. The extract was centrifuged and the absorbance of the supernatant was measured at 620 nm with a spectrophotometer. The dye concentration in the extracts was calculated from a standard curve of Evans blue in formamide and normalized to the dry tissue weight.

Statistical Analysis

Vessel density counts, tumor volume and tumor weight were analysed using the Mann-Whitney's t test. Analyses were computed using the statistical software StatView (Abacus Concepts Inc, Berkeley, Calif., USA).

Results

JAM-C is Expressed by Tumor Vessels and is Receptive to Angiogenic Stimuli

Figure 2A:
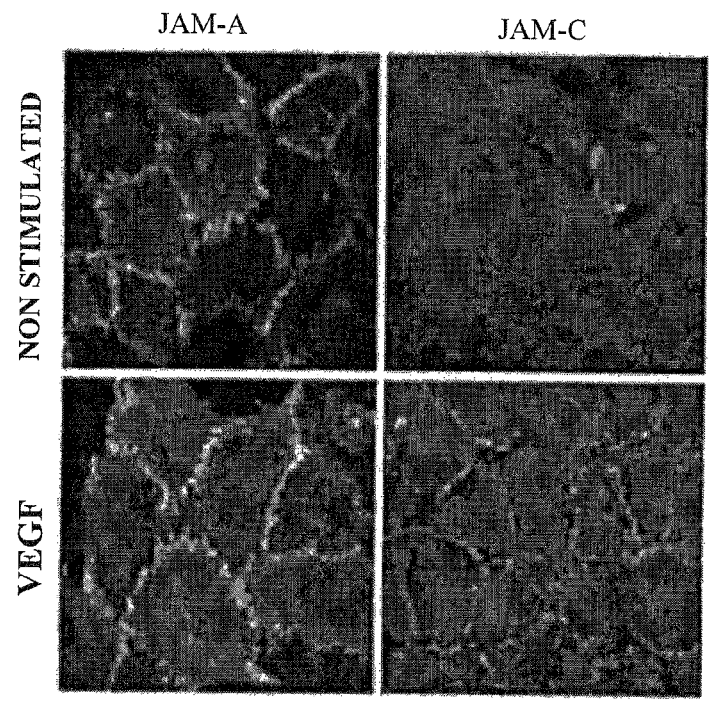
FIG. 2 demonstrates that JAM-C is recruited at inter-endothelial junctions of HUVECs upon VEGF stimulation. (A) HUVECs were stimulated with recombinant VEGF-165, fixed with formaldehyde and JAM-C localization was visualized with anti-JAM-C monoclonal antibody. As control, JAM-A staining was performed. The JAM-C molecule was enriched at cell-cell contacts upon VEGF-165 stimulation whereas no effect was seen with JAM-A. (B) FACS analysis revealed that the enrichment of JAM-C at cell-cell contacts is due to relocalization of the molecule since the expression level remained unchanged after VEGF treatment (thin line, negative control; dashed line, non treated cells; thick line, VEGF treated cells).
Figure 2B:
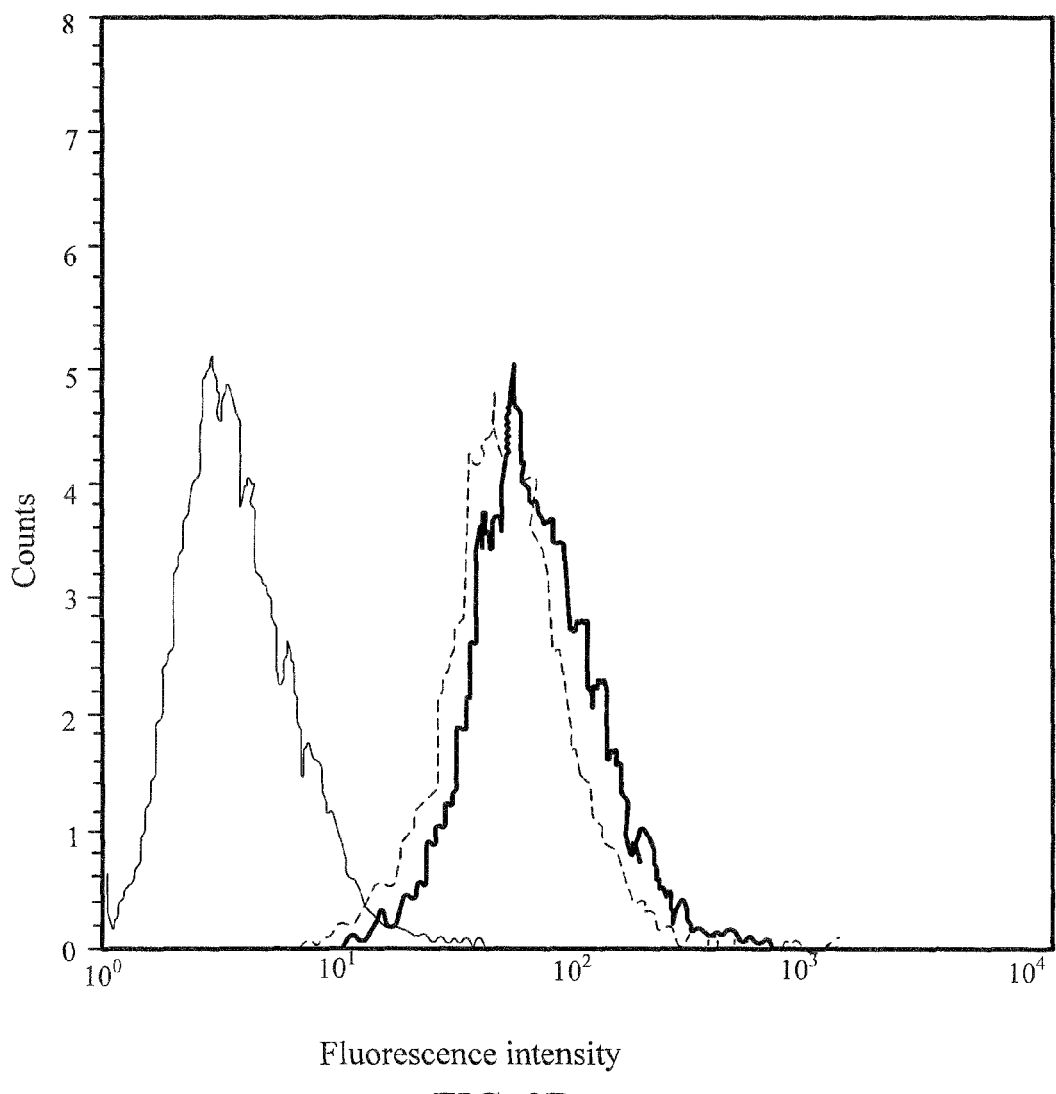

In angiogenic tumor of human liver, anti-JAM-C antibody H36 stains blood vessels (FIG. 1). In contrast, the transcript encoding JAM-C is not present in normal liver. Treatment of HUVECs with VEGF leads to immediate and massive accumulation of JAM-C in endothelial cell-cell contacts within 15 minutes (FIG. 2A). This short appearance is the result of JAM-C relocalization and the expression level is not modified by this treatment (FIG. 2B). The same results were observed when HUVECs were simulated with TNF-α or thrombin.

In Vitro Vessel Outgrowth is Inhibited by Anti-Jam-C Monoclonal Antibody

Figure 3:
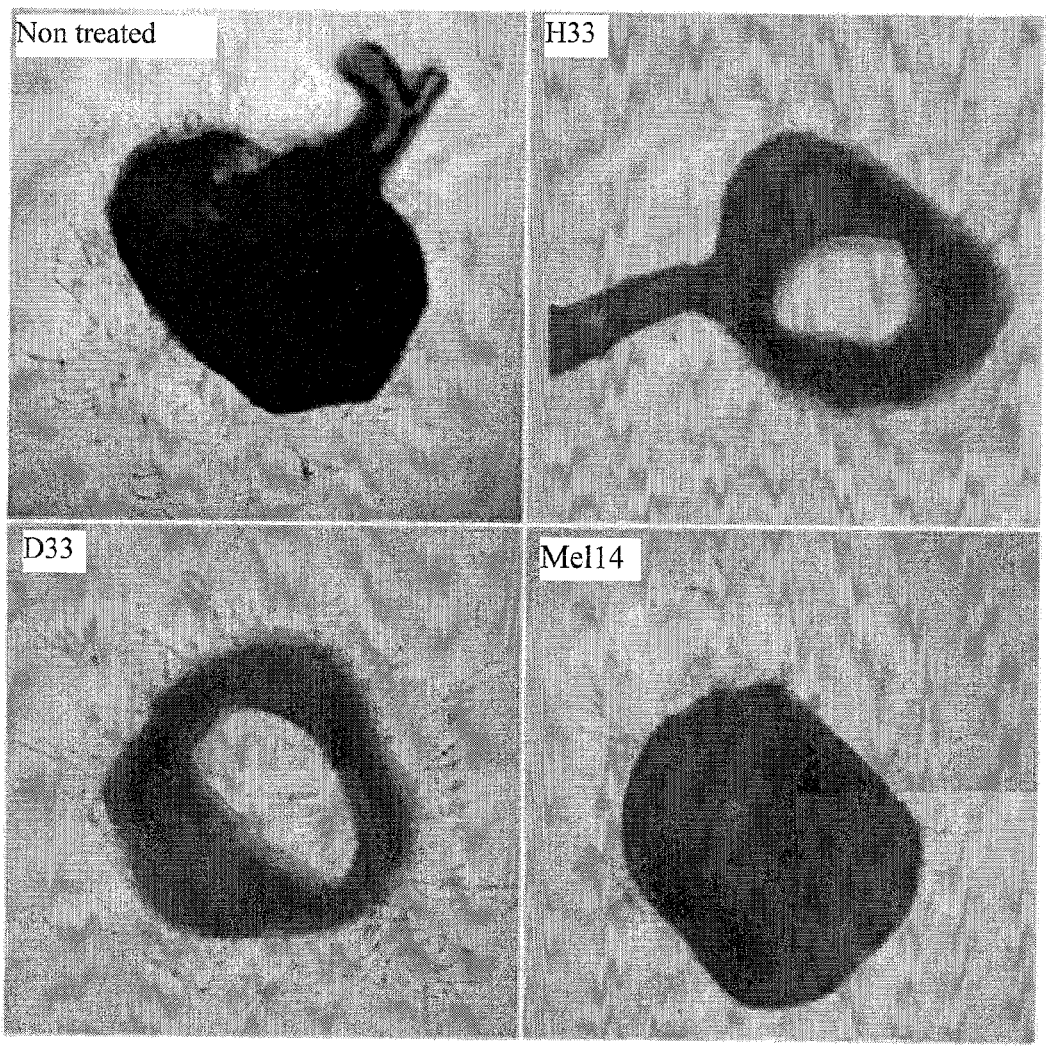
FIG. 3 demonstrates that anti-JAM-C monoclonal antibody abolished angiogenesis in vitro. Aortic rings from mice were grown between two Matrigel layers in the presence or absence of anti-JAM-C antibodies (50 μg/ml) and neovascularization was visualized after 12 days. Pictures are light micrographs of representative non treated (A, n=11) or treated aortic ring microvessels with anti-JAM-C monoclonal antibodies H33 (B, n=11) and D33 (C, n=6) or isotype-matched control antibody Mel14 (D, n=6). Only H33 blocked angiogenic sprouting.

In vitro neovascularization was carried out using ex vivo aortic rings assays. Freshly dissected mouse aortae were cut into small rings and those embedded in Matrigel in the presence or absence of anti-JAM-C antibodies. Outgrowth of endothelial vessels from the aortic rings were assessed over a period of 12 days. Whereas the presence of control anti-JAM-C or isotype matched antibodies do not affect aortic sprouting, the H33 anti-JAM-C antibody totally blocks neovascularization (FIG. 3).

Anti Jam-C Monoclonal Antibody Reduces Tumor Growth and Angiogenesis In Vivo

Given that in vitro angiogenesis can be blocked with H33 anti-JAM-C antibody, we investigated whether this antibody had an effect on tumor angiogenesis and tumor growth. Mice were subcutaneously injected with. Lewis lung carcinoma cells. Anti-JAM-C and control antibodies were then injected intraperitoneally every second day. Animals were sacrificed when the control tumors reached 1-1.5 $cm^3$ and tumors excised. Tumor size (FIG. 4A), volume (FIG. 4B) and weight (FIG. 4C) were significantly decreased when mice were treated with H33 anti-JAM-C antibody compared with the control isotype matched antibody or PBS.

Figure 4A:
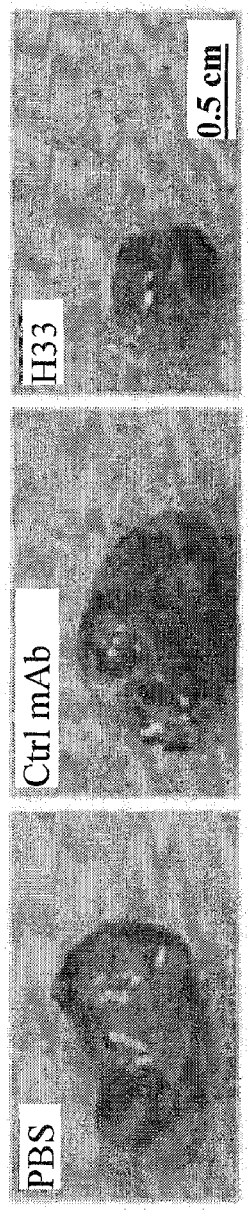
FIG. 4 demonstrates that anti-JAM-C antibody H33 reduced tumor growth and tumor vascularization. Mice were injected sub-cutaneously with LLC1 tumor cells and treated every second day with anti-JAM-C antibody or isotype-matched control antibody (150 μg). (A) macroscopic appearance of 12-day-old LLC1 tumors grown in control mice (PBS and isotype-matched control antibody) or in mice treated with H33 anti-JAM-C antibody. Mice treated with H33 anti-JAM-C antibody show reduced tumor growth as indicated by measurement of tumor volume (B) and tumor weight (C). Microvessels were detected by PECAM-1 immunostaining (D) and quantified by computer analysis (E).*p<0,01. Each bar represents the mean value of ten animals tested±sem.
Figure 4B:
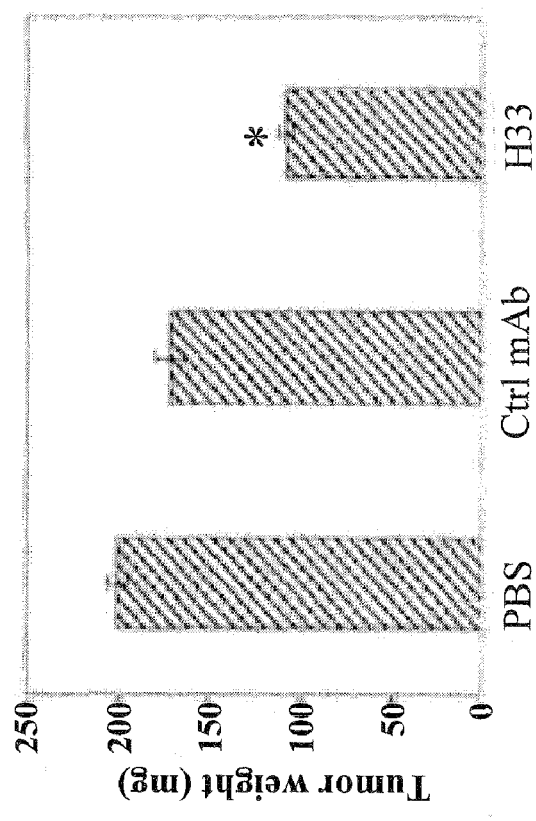
Figure 4C:
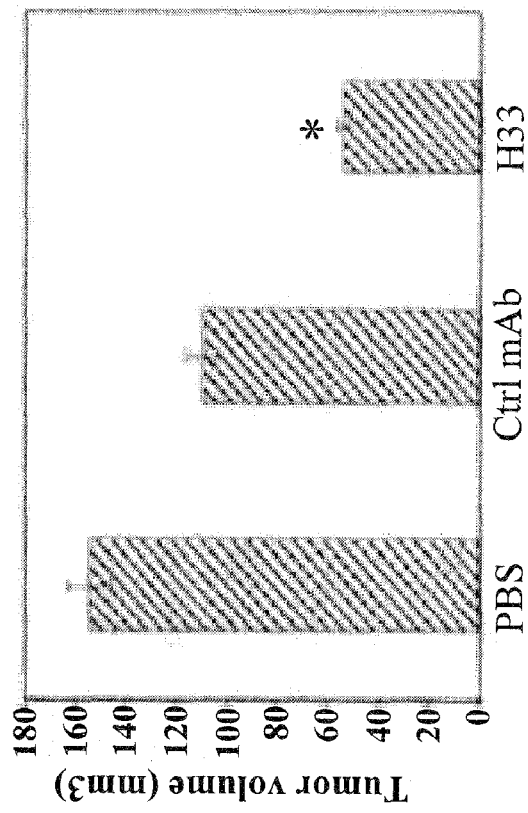
Figure 4E:
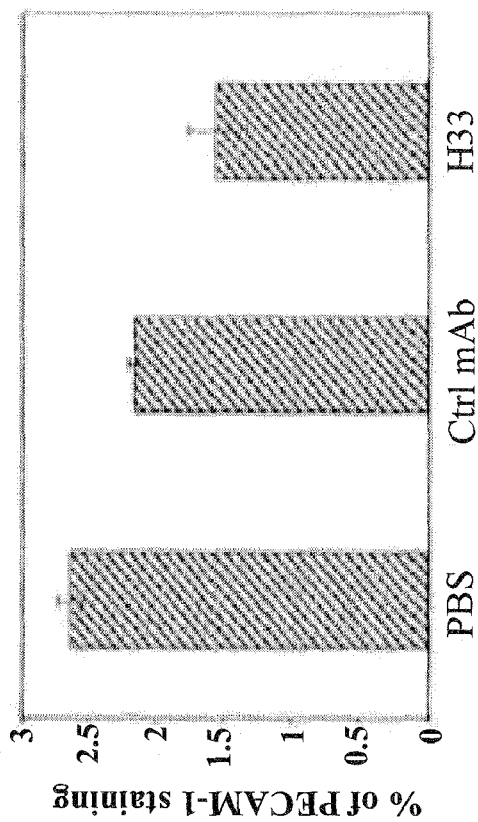
Figure 4D:
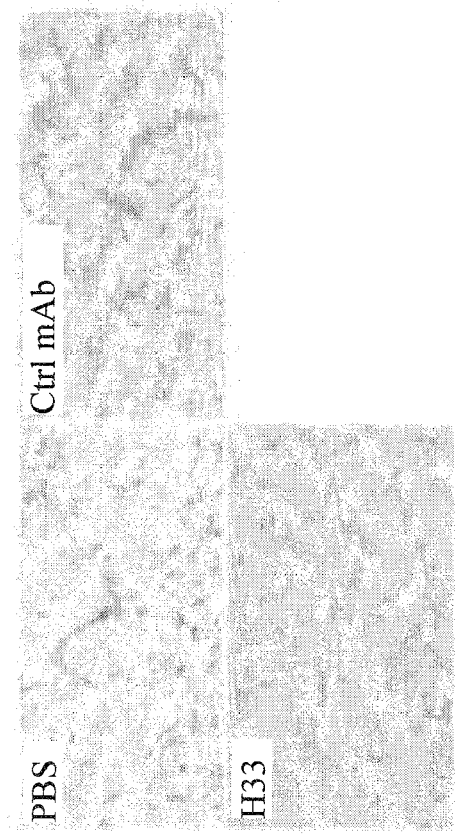

Representative examples of excised tumors are shown in FIG. 4A. Lewis lung carcinoma cells do not express JAM-C (data not shown). The H33 antibody effect on tumor growth is due to inhibition of angiogenesis. In order to visualize the tumor vasculature, cryosections were immunostained with antibody against the endothelial marker PECAM-1 (FIG. 4D). Blood vessel density was quantified by counting the % of PECAM-1 staining across the area of the tumor (FIG. 4E). The H33 antibody reduced the number of blood vessels in tumors when compared to the controls.

H33 anti-JAM-C Monoclonal Antibody is not Toxic In Vivo

Figure 5A:
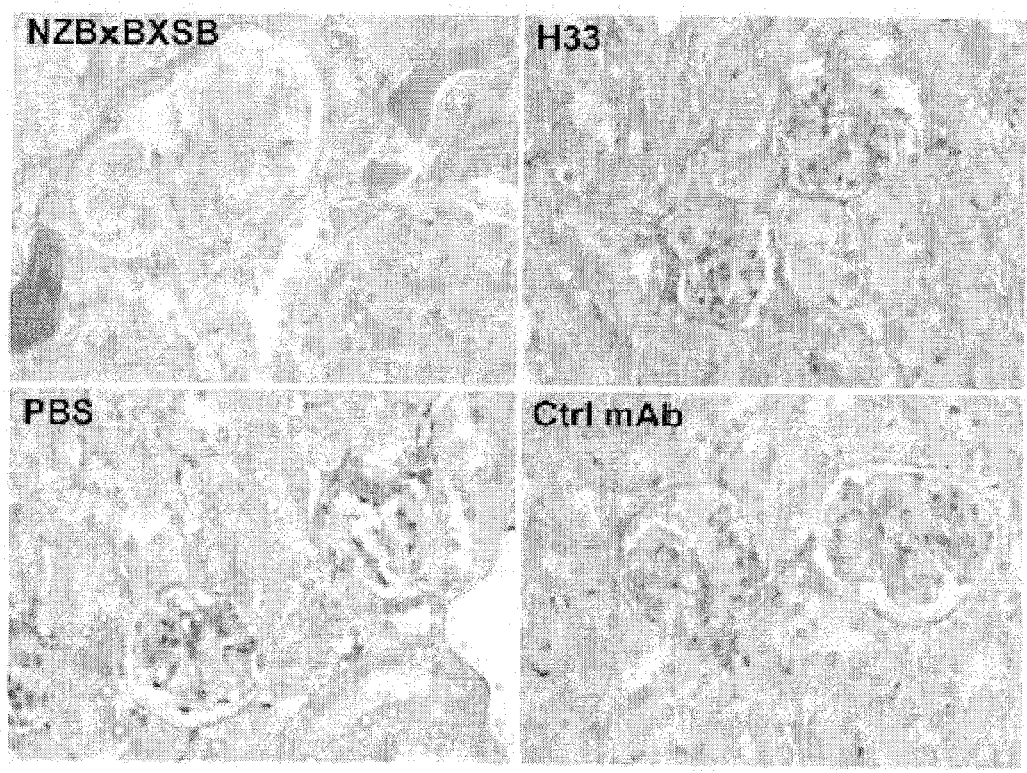
FIG. 5 demonstrates that H33 anti-JAM-C antibody is not toxic in vivo. To ensure that the H33 anti-JAM-C antibody effect on tumor growth was not due to a general toxic effect in vivo, mice were treated as described in FIG. 4 and the organs dissected and analysed. (A) Kidney from these mice stained with periodic acid-Schiff (PAS) did not show any signs of glomerulonephritis development. As control, sections of kidney from autoimmune diseased NZBxBXSB mice were compared (Merino R. et al., J din Invest. 94(2):521-5 (1994). (B) In vivo blood vessel permeability was assessed using the Evans blue permeability assay. The H33 antibody had no effect on vascular permeability in the representative organs heart, lung, kidney and brain. Each bar represents the mean value of seven animals tested± sem.

It is known that antibodies can be toxic when injected in vivo. In order to control that the observed effect of H33 anti-JAM-C antibody is not due to a general toxic effect in mice it was investigated whether antibody injected animals develop pathologies. Since JAM-C is expressed by endothelium in the kidney it was first analysed whether the antibody would create glomerulonephritis. To this end kidney sections of treated animals were stained with periodic acid-Schiff. No abnormal accumulation of protein in glomeruli was detected (FIG. 5A).

Figure 5B:
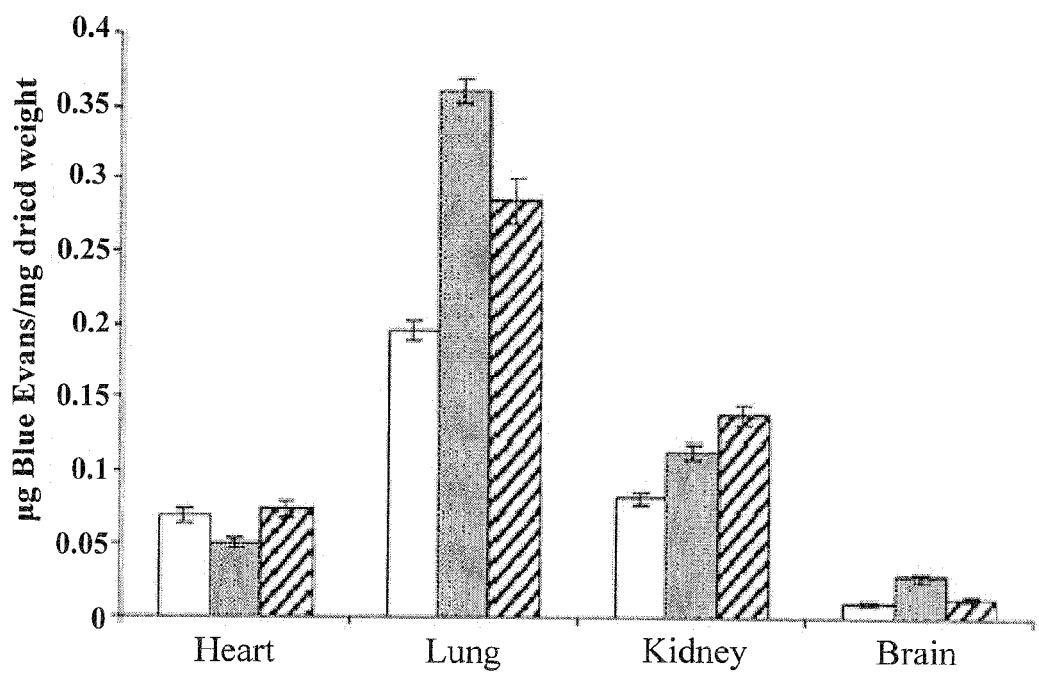

Since JAM-C is involved in controlling vascular permeability it was also tested whether the antibody would induce leakiness of blood vessels., Fortunately this was not the case in heart, lung, kidney or brain, the representative organs analysed (FIG. 5B).

Figure 6:
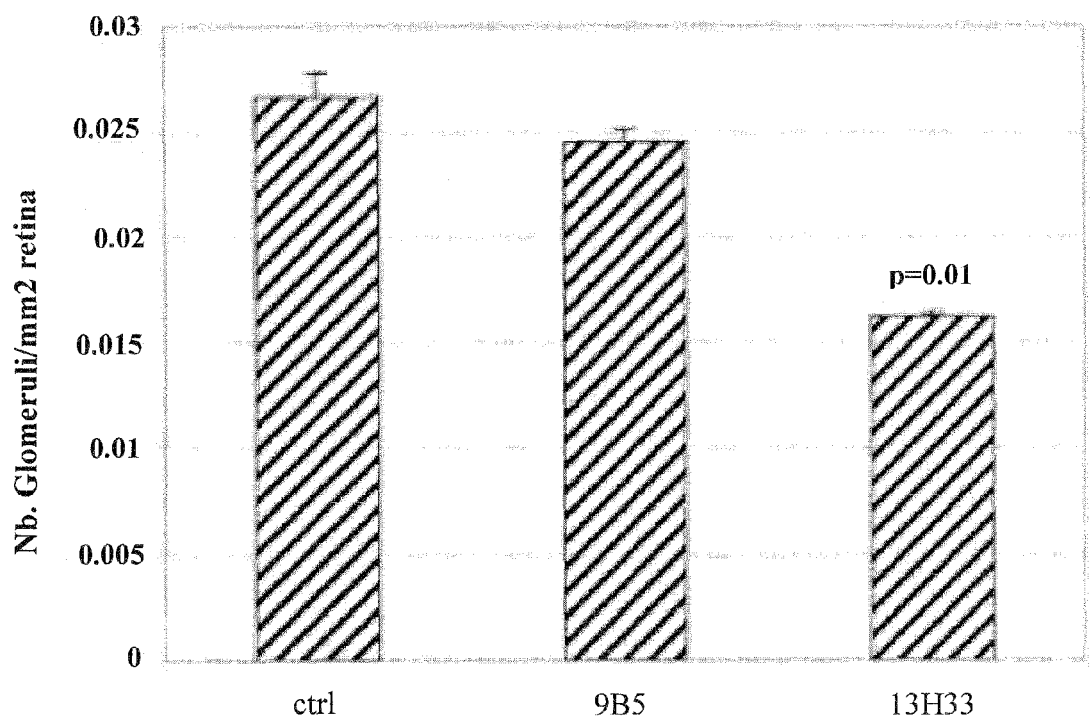
FIG. 6 demonstrates quantitation of glomeruli during revascularization of retinas. The numbers of glomeruli were counted to compare retinal neovascularization in H33-treated and control antibody-treated mice. Reduction in the number of glomeruli was observed in H33 treated (13H33) compared to control mice (ctrl) or mice treated with isotype matched control antibody (9B5). This indicates a decreased neovascularization of retinas in H33 treated animals.

Reduction in the number of glomeruli was observed in H33 treated compared to control mice (ctrl) or mice treated with isotype matched control antibody. This indicates a decreased neovascularization of retinas in H33 treated animals (FIG. 6).

We claim:

1. A method for detecting JAM-C in a biological sample comprising the steps of:
   a) obtaining a biological sample;
   b) exposing said biological sample to a specific antibody; and
   c) detecting binding of said specific antibody in said biological sample to JAM-C, wherein said specific antibody is: a) monoclonal antibody H33, produced by hybridoma 13H33 as deposited with the Deutsche Sammlung von Mikroorganismen and Zellkulturen GmbH under the deposit accession number DSM ACC2622, b) isolated antigen binding fragments of the antibody H33, or c) a recombinant antibody that comprises all of the CDRs of the H33 antibody.

2. The method according to claim 1, wherein said recombinant antibody or said isolated antigen binding fragments of said antibody H33 are:
   a) a Fab fragment;
   b) a Fv fragment comprising all of said CDRs of the heavy and light chains of said H33 antibody; or
   c) a scFv, a dimer of a scFv, a trimer of a scFv or a larger aggregate of a scFv, at least one of said scFv comprising all of said CDRs of said H33 antibody.

3. The method according to claim 1, wherein said recombinant antibody is:
   a) a humanized antibody comprising all of said CDRs of said H33 antibody; or
   b) a chimeric antibody comprising all of said CDRs of said H33 antibody.

4. The method according to claim 1, wherein said antibody is the monoclonal antibody H33, produced by hybridoma 13H33 as deposited with the Deutsche Sammlung von Mikroorganismen und Zellkulturen GmbH under the deposit accession number DSM ACC2622.

5. The method according to claim 1, wherein said antibody is an isolated antigen binding fragment of said antibody H33.

6. The method according to claim 1, wherein said recombinant antibody is a recombinant antibody comprising all of said CDRs of said H33 antibody.

7. The method according to claim 1, wherein said isolated antigen binding fragments of said antibody H33 are Fab fragments.

8. The method according to claim 1, wherein said recombinant antibody is a Fv fragment and comprises all of said CDRs of said H33 antibody.

9. The method according to claim 1, wherein said recombinant antibody is a scFv, a dimer of a scFv, a trimer of a scFv or a larger aggregate of a scFv, at least one of said scFv comprising all of said CDRs of said H33 antibody.

10. The method according to claim 1, wherein said recombinant antibody is a humanized antibody and comprises all of said CDRs of said H33 antibody.

11. The method according to claim 1, wherein said recombinant antibody is a chimeric antibody and comprises all of said CDRs of said H33 antibody.

12. The method according to claim 1, wherein said isolated antigen binding fragments of said antibody H33 comprise:
   a) a $V_{HH}$ comprising all of the heavy chain CDRs of said H33 antibody; or
   b) a single domain antigen binding fragment comprising all of the heavy chain CDRs of said H33 antibody produced by hybridoma 13H33 deposited as DSM ACC2662.

* * * * *

UNITED STATES PATENT AND TRADEMARK OFFICE
CERTIFICATE OF CORRECTION

| | | |
|---|---|---|
| PATENT NO. | : 8,093,010 B2 | Page 1 of 1 |
| APPLICATION NO. | : 12/608029 | |
| DATED | : January 10, 2012 | |
| INVENTOR(S) | : Beat A. Imhof et al. | |

It is certified that error appears in the above-identified patent and that said Letters Patent is hereby corrected as shown below:

Column 4,
Line 53, "J. din Invest." should read --J. Clin Invest.--.

Column 8,
Line 27, "147-156" should read --147-158--.
Line 41, "$^{111}$rhenium" should read --$^{111}$Indium--.

Column 15,
Line 2, "trofosfamide" should read --trofosfarnide--.
Line 7, "caminomycin" should read --carminomycin--.

Column 21,
Line 47, "JAM-E or JAM-C" should read --JAM-B or JAM-C--.

Column 24,
Line 40, "435-497" should read --495-497--.

Signed and Sealed this
Twenty-second Day of May, 2012

David J. Kappos
*Director of the United States Patent and Trademark Office*